US008926946B2

(12) United States Patent
Muro Galindo et al.

(10) Patent No.: US 8,926,946 B2
(45) Date of Patent: Jan. 6, 2015

(54) PEPTIDES FOR TRANSPORT OF THERAPEUTICS AND THEIR CARRIERS IN MOUSE MODELS AND HUMANS

(75) Inventors: Silvia Muro Galindo, Silver Spring, MD (US); Ming Meng, Baoding (CN); Carmen Garnacho Montero, Sevilla (ES)

(73) Assignee: University of Maryland, College Park, College Park, MD (US)

( * ) Notice: Subject to any disclaimer, the term of this patent is extended or adjusted under 35 U.S.C. 154(b) by 26 days.

(21) Appl. No.: 13/376,362

(22) PCT Filed: Jun. 4, 2010

(86) PCT No.: PCT/US2010/037490

§ 371 (c)(1), (2), (4) Date: Dec. 5, 2011

(87) PCT Pub. No.: WO2010/141879

PCT Pub. Date: Dec. 9, 2010

(65) Prior Publication Data

US 2012/0076730 A1 Mar. 29, 2012

Related U.S. Application Data

(60) Provisional application No. 61/220,404, filed on Jun. 25, 2009, provisional application No. 61/184,657, filed on Jun. 5, 2009.

(51) Int. Cl.

| | |
|---|---|
| ***A61K 31/7088*** | (2006.01) |
| ***A61K 49/00*** | (2006.01) |
| ***C12N 5/071*** | (2010.01) |
| ***C12Q 1/02*** | (2006.01) |
| ***A61K 38/02*** | (2006.01) |
| ***A61K 31/70*** | (2006.01) |
| ***A61K 35/76*** | (2006.01) |
| ***A61K 35/74*** | (2006.01) |
| ***A61K 35/00*** | (2006.01) |
| ***A61K 38/43*** | (2006.01) |
| ***A61K 9/46*** | (2006.01) |
| ***C07K 7/08*** | (2006.01) |
| ***C07K 7/06*** | (2006.01) |
| ***C12N 15/12*** | (2006.01) |
| ***C12N 15/11*** | (2006.01) |
| ***C12N 15/63*** | (2006.01) |
| ***A61P 3/10*** | (2006.01) |
| ***A61P 29/00*** | (2006.01) |
| ***A61P 35/00*** | (2006.01) |
| ***A61P 37/00*** | (2006.01) |
| ***A61P 7/02*** | (2006.01) |
| ***A61P 11/00*** | (2006.01) |
| ***A61P 9/10*** | (2006.01) |
| ***A61P 9/12*** | (2006.01) |
| ***A61K 47/42*** | (2006.01) |
| ***A61K 9/127*** | (2006.01) |
| ***A61K 9/16*** | (2006.01) |
| ***A61K 9/50*** | (2006.01) |
| ***A61K 9/51*** | (2006.01) |
| ***A61K 38/47*** | (2006.01) |
| ***A61K 47/48*** | (2006.01) |
| ***A61K 51/12*** | (2006.01) |
| ***C07K 16/28*** | (2006.01) |
| *B82Y 5/00* | (2011.01) |
| *A61K 39/00* | (2006.01) |

(52) U.S. Cl.

CPC ............ *A61K 9/1273* (2013.01); *A61K 9/1605* (2013.01); *A61K 9/5094* (2013.01);

(Continued)

(58) Field of Classification Search

CPC ............ A61K 2039/505; A61K 38/47; A61K 47/48176; A61K 47/482; A61K 47/48215; A61K 47/48246; A61K 47/48561; A61K 51/1203; A61K 9/1273; A61K 9/1605; A61K 9/5094; A61K 9/5107; C07K 16/2821; C07K 2317/77

See application file for complete search history.

(56) References Cited

U.S. PATENT DOCUMENTS 5,599,790 A * 2/1997 Altieri et al. ................ 514/13.6
6,737,058 B2 5/2004 Altieri et al.

FOREIGN PATENT DOCUMENTS

WO 2006007560 A2 1/2006
WO 2007024817 A2 3/2007

(Continued)

OTHER PUBLICATIONS

Muro et al. Molecular Therapy. 13(1);135-141:2006.*

(Continued)

*Primary Examiner* — Karlheinz R Skowronek
*Assistant Examiner* — Schuyler Milton
(74) *Attorney, Agent, or Firm* — Hultquist, PLLC; Mary B. Grant

(57) ABSTRACT

A system for targeted delivery of agents (e.g., molecular probes, diagnostic agents, therapeutic agents, imaging agents, research or analytical compounds, enzymes, peptides, proteins, lipids, lipoproteins, sugars, hormones, vitamins, nucleic acids, viruses, bacteria, and/or cells) including use of a composition containing the agent and a targeting moiety, specific for a determinant at the target location. An exemplary composition of the system includes a targeting moiety of one of peptides γ3, 2γ3, 3γ3, A1, B7, B8, B9, B1O, and D6, specific for targeting ICAM-I. The system enables effective, versatile, and safe targeting and transport of agents. The system is useful in research applications, as well as in the context of translational science and clinical interventions.

22 Claims, 12 Drawing Sheets

(52) U.S. Cl.
CPC .............. *A61K 9/5107* (2013.01); *A61K 38/47* (2013.01); *A61K 47/48176* (2013.01); *A61K 47/482* (2013.01); *A61K 47/48215* (2013.01); *A61K 47/48246* (2013.01); *A61K 47/48561* (2013.01); *A61K 51/1203* (2013.01); *C07K 16/2821* (2013.01); *A61K 2039/505* (2013.01); *C07K 2317/77* (2013.01); *Y10S 977/773* (2013.01); *Y10S 977/906* (2013.01)
USPC ............ 424/9.1; 514/773; 514/44 R; 514/1.1; 514/23; 435/375; 435/29; 435/320.1; 424/93.6; 424/93.4; 424/93.1; 424/94.1; 424/450; 424/94.6; 530/326; 530/329; 536/23.5; 536/23.1; 977/773; 977/906

(56) References Cited

FOREIGN PATENT DOCUMENTS

| | | |
|---|---|---|
| WO | 2008147526 A1 | 12/2008 |
| WO | 2010141879 A2 | 12/2010 |

OTHER PUBLICATIONS

Garnacho, C., et al., "Differential intra-endothelial delivery of polymer nanocarriers targeted to distinct PECAM-1 epitopes", "Journal of Controlled Release", Jun. 18, 2008, pp. 226-233, vol. 130.
Murciano, J., et al., "ICAM-directed vascular immunotargeting of antithrombotic agents to the endothelial luminal surface", "Blood", Jan. 16, 2003, pp. 3977-3984, vol. 101, No. 10.
Muro, S., et al., "A novel endocytic pathway induced by clustering endothelial ICAM-1 or PECAM-1", "Journal of Cell Science", 2003, pp. 1599-1609, vol. 116.
Muro, S, et al., "Control of Endothelial Targeting and Intracellular Delivery of Therapeutic Enzymes by Modulating the Size and Shape of ICAM-1-targeted Carriers", "Mol Ther.", Aug. 2008, pp. 1450-1458, vol. 16, No. 8.
Altieri, D., et al., "Structural Recognition of a Novel Fibrinogen y Chain Sequence (117-133) by Intercellular Adhesion Molecule-1 Mediates Leukocyte-Endothelium Interaction", "The Journal of Biological Chemistry", Jan. 13, 1995, pp. 696-699, vol. 270, No. 2
Anderson, M., et al., "Mechanism of Binding and Internalization of ICAM-1-Derived Cyclic Peptides by LFA-1 on the Surface of T Cells: A Potential Method for Targeted Drug Delivery", "Pharmaceutical Research", Oct. 2003, pp. 1523-1532, vol. 20, No. 10.
Belizaire, A., et al., "Identification of a murine ICAM-1-specific peptide by subtractive phage library selection on cells", "Biochemical and Biophysical Research Communications", 2003, pp. 625-630, vol. 309.
Chittasupho, C., et al., "ICAM-1 targeting of doxorubicin-loaded PLGA nanoparticles to lung epithelial cells", "European Journal of Pharmaceutical Sciences", Feb. 27, 2009, pp. 141-150, vol. 37.
D'Souza, S., et al., "Identification of an Active Sequence within the First Immunoglobulin Domain of Intercellular Cell Adhesion Molecule-1 (ICAM-1) That Interacts with Fibrinogen", "The Journal of Biological Chemistry", Sep. 27, 1996, pp. 24270-24277, vol. 271, No. 39.
Duperray, A., et al., "Molecular Identification of a Novel Fibrinogen Binding Site on the First Domain of ICAM-1 Regulating Leukocyte-Endothelium Bridging", "The Journal of Biological Chemistry", Jan. 3, 1997, pp. 435-441, vol. 272, No. 1.
Hayashi, T., et al., "MUC1 Mucin Core Proteins Binds to the Domain 1 of ICAM-1", "Digestion", 2001, pp. 87-92, vol. 63 (Suppl 1).
He, X., et al., "A fluorescence-based, high-performance liquid chromatographic assay to determine acid sphingomyelinase activity and diagnose types A and B Niemann—Pick disease", "Analytical Biochemistry", 2003, pp. 116-120, vol. 314.
Jaafari, M., et al., "Targeting of Liposomes to Human Keratinocytes Through Adhesive Peptides from Immunoglobulin Domains in the Presence of IFN-gamma", "Drug Delivery", 2002, pp. 1-9, vol. 9.
Kam, J., et al., "MUC1 Synthetic Peptide Inhibition of Intercellular Adhesion Molecule-1 and MUC1 Binding Requires Six Tandem Repeats", "Cancer Research", Dec. 1, 1998, pp. 5577-5581, vol. 58.
Languino, L., et al., "Fibrinogen Mediates Leukocyte Adhesion to Vascular Endothelium through an ICAM-1-Dependent Pathway", "Cell", Jul. 2, 1993, pp. 1423-1434, vol. 73.
Muro, S., et al., "Endothelial Endocytic Pathways: Gates for Vascular Drug Delivery", "Current Vascular Pharmacology", 2004, pp. 281-299, vol. 2.
Muro, S., "Chapter 117 Intercellular Adhesion Molecule-1 and Vascular Cell Adhesion Molecule-1", "The Endothelium: A Comprehensive Reference (W. Aird, Ed.)", Jan. 19, 2007, pp. 1058-1070, Publisher: Cambridge University Press, Published in: New York.
Muro, S., et al., "Slow intracellular trafficking of catalase nanoparticles targeted to ICAM-1 protects endothelial cells from oxidative stress", "Am J Physiol Cell Physiol", Jul. 23, 2003, pp. C1339-C1347, vol. 285.
Muro, S., et al., "ICAM-1 recycling in endothelial cells: a novel pathway for sustained intracellular delivery and prolonged effects of drugs", "Blood", Sep. 14, 2004, pp. 650-658, vol. 105, No. 2.
Muro, S., et al., "Control of intracellular trafficking of ICAM-1-targeted nanocarriers by endothelial Na+/H+ exchanger proteins", "Am J Physiol Lung Cell Mol Physiol", Nov. 18, 2005, pp. L809-L817, vol. 290.
Muro, S., et al., "Lysosomal Enzyme Delivery by ICAM-1-Targeted Nanocarriers Bypassing Glycosylation- and Clathrin-Dependent Endocytosis", "Molecular Therapy", Sep. 8, 2005, pp. 135-141, vol. 13, No. 1.
Muro, S., et al., "Endothelial Targeting of High-Affinity Multivalent Polymer Nanocarriers Directed to Intercellular Adhesion Molecule 1", "The Journal of Pharmacology and Experimental Therapeutics", 2006, pp. 1161-1169, vol. 317, No. 3.
Pardridge, W., "Molecular Trojan horses for blood-brain barrier drug delivery", "Current Opinion in Pharmacology", Jul. 12, 2006, pp. 494-500, vol. 6.
Rothlein, R., et al., "A Human Intercellular Adhesion Molecule (ICAM-1) Distinct From LFA-1", "The Journal of Immunology", Aug. 15, 1986, pp. 1270-1274, vol. 137, No. 4.
Schnitzer, J., "Caveolae: from basic trafficking mechanisms to targeting transcytosis for tissue-specific drug and gene delivery in vivo", "Advanced Drug Delivery Reviews", 2001, pp. 265-280, vol. 49.
Schuchman, E., et al., "Chapter 8 The Development of Enzyme Replacement Therapy for Lysosomal Diseases: Gaucher Disease and Beyond", "Gaucher disease: Lessons learned about therapy of lysosomal disorders (Futerman, A., Ed.)", Jun. 1, 2006, pp. 125-140, Publisher: CRC Press.
Sillerud, L., et al., "NMR solution structure of a potent cyclic nonapeptide inhibitor of ICAM-1-mediated leukocyte adhesion produced by homologous amino acid substitution", "J. Peptide Res.", 2004, pp. 127-140, vol. 64.
Smith, J., et al., "Identification of a *Plasmodium faciparum* intercellular adhesion molecule-1 binding domain: A parasite adhesion trait implicated in cerebral malaria", "PNAS", Feb. 15, 2000, pp. 1766-1771, vol. 97, No. 4.
Springer, A., et al., "Functional interdependence of the DBLbeta domain and c2 region for binding of the *Plasmodium falciparum* variant antigen to ICAM-1", "Molecular and Biochemical Parasitology", May 25, 2004, pp. 55-64, vol. 137.
Weisel, J., "Fibrinogen and Fibrin", "Advances in Protein Chemistry", 2005, pp. 247-299, vol. 70.
Welply, J., et al., "A Peptide Isolated by Phage Display Binds to ICAM-1 and Inhibits Binding to LFA-1", "Proteins: Structure, Function, and Genetics", 1996, pp. 262-270, vol. 26.
Xu, C., et al., "Structural and ICAM-1-Docking Properties of a Cyclic Peptide from the I-domain of LFA-1: An inhibitor of ICAM-1/LFA-1-mediated T-cell adhesion", "Journal of Biomolecular Structure and Dynamics", 2002, pp. 789-799, vol. 19, No. 5.
Note: For the non-patent literature citations that no month of publication is indicated, the year of publication is more than 1 year prior to the effective filing date of the present application.

(56) References Cited

OTHER PUBLICATIONS

Gardiner, E., et al., "A Mitogenic Action for Fibrinogen Mediated through Intercellular Adhesion Molecule-1", "The Journal of Biological Chemistry", Jun. 13, 1997, pp. 15474-15480, vol. 272, No. 24.

Garnacho, C., et al., "A Fibrinogen-Derived Peptide Provides Intercellular Adhesion Molecule-1-Specific Targeting and Intraendothelial Transport of Polymer Nanocarriers in Human Cell Cultures and Mice", "The Journal of Pharmacology and Experimental Therapeutics", Mar. 2012, pp. 638-647, vol. 340, No. 3.

Ansar, M., et al., "Biological Functionalization of Drug Delivery Carriers to Bypass Size Restrictions of Receptor-Mediated Endocytosis Independently from Receptor Targeting", "ACS Nano", Nov. 15, 2013, pp. 10597-10611, vol. 7, No. 12

Garnacho, C., et al., "Delivery of Acid Sphingomyelinase in Normal and Niemann-Pick Disease Mice Using Intercellular Adhesion Molecule-1-Targeted Polymer Nanocarriers", "The Journal of Pharmacology and Experimental Therapeutics", Feb. 20, 2008, pp. 400-408, vol. 325, No. 2

Guo, H., et al., "Effects of the Amino Acid Linkers on the Melanoma-Targeting and Pharmacokinetic Properties of 111In-Labeled Lactam Bridge—Cyclized alpha-MSH Peptides", "The Journal of Nuclear Medicine", Mar. 18, 2011, vol. 52, No. 4

Papademetriou, J., et al., "Comparative binding, endocytosis, and biodistribution of antibodies and antibody-coated carriers for targeted delivery of lysosomal enzymes to ICAM-1 versus transferrin receptor", "Journal of Inherited Metabolic Disease", Sep. 12, 2012, pp. 467-477, vol. 36, No. 3.

Papademetriou, I., et al., "In vivo performance of polymer nanocarriers dually-targeted to epitopes of the same or different receptors", "Biomaterials", Feb. 9, 2013, pp. 3459-3466, vol. 34, No. 2013.

Perche, F., et al., "Recent Trends in Multifunctional Liposomal Nanocarriers for Enhanced Tumor Targeting", "Journal of Drug Delivery", Mar. 7, 2013, pp. 1-32 pages, vol. 2013, No. Article ID 705265.

Reilly, P., et al., "The Native Structure of Intercellular Adhesion Molecule-1 (ICAM- 1) is a Dimer", "The Journal of Immunology", Jul. 15, 1995, pp. 529-532, vol. 155, No. 2.

Shiokawa, T., et al., "Effect of Polyethylene Glycol Linker Chain Length of Folate-Linked Microemulsions Loading Aclacinomycin A on Targeting Ability and Antitumor Effect In vitro and In vivo", "Clinical Cancer Research", Mar. 1, 2005, pp. 2018-2025, vol. 11, No. 5

Stefanick, J., et al., "A Systematic Analysis of Peptide Linker Length and Polyethylene Glycol Coating on Cellular Uptake of Peptide-Targeted Liposomes", "ACS Nano", Mar. 5, 2013, pp. 2935-2947 (Abstract), vol. 7, No. 4.

Boyd, J., et al., "Fibrinogen decreases cardiomyocyte contractility through an ICAM-1-dependent mechanism", "Critical Care", Jan. 2008, p. R2, vol. 12, No. 1.

Kim, S., et al., "Fibrinogen binding to ICAM-1 promotes EGFR-dependent mucin production in human airway epithelial cells", "Am J Physiol Lung Cell Mol Physiol", May 2009, pp. L174-L183, vol. 297, No. 1.

Tsakadze, N., et al., "Interactions of Intercellular Adhesion Molecule-1 with Fibrinogen", "Trends Cardiovascular Medicine", Apr. 2002, p. 101-108, vol. 12, No. 3.

* cited by examiner

C

| Specificity Index | γ3/ASM | 2γ3/ASM | 3γ3/ASM |
|---|---|---|---|
| Kidneys | 3.4 | 2.1 | 2.6 |
| Spleen | 11.8 | 7.5 | 4.4 |
| Heart | 9.3 | 7.0 | 8.1 |
| Lungs | 187.7 | 106 | 97.6 |
| Liver | 2.4 | 0.9 | 1.2 |
| Brain | 4.7 | 7.7 | 8.0 |

SEQUENCE LISTING

```
<160> NUMBER OF SEQ ID NOS: 31

<210> SEQ ID NO 1
<211> LENGTH: 17
<212> TYPE: PRT
<213> ORGANISM: Artificial Sequence
<220> FEATURE:
<223> OTHER INFORMATION: fibrinogen-derived gamma-3

<400> SEQUENCE: 1

Asn Asn Gln Lys Ile Val Asn Leu Lys Glu Lys Val Ala Gln Leu Glu
1               5                   10                  15

Ala


<210> SEQ ID NO 2
<211> LENGTH: 17
<212> TYPE: PRT
<213> ORGANISM: Artificial Sequence
<220> FEATURE:
<223> OTHER INFORMATION: fibrinogen-derived 2-gamma-3

<400> SEQUENCE: 2

Asn Asn Gln Lys Ile Val Asn Ile Lys Glu Lys Val Ala Gln Ile Glu
1               5                   10                  15

Ala


<210> SEQ ID NO 3
<211> LENGTH: 17
<212> TYPE: PRT
<213> ORGANISM: Artificial Sequence
<220> FEATURE:
<223> OTHER INFORMATION: fibrinogen-derived 3-gamma-3

<400> SEQUENCE: 3

Asn Asn Gln Lys Leu Val Asn Ile Lys Glu Lys Val Ala Gln Ile Glu
1               5                   10                  15

Ala


<210> SEQ ID NO 4
<211> LENGTH: 60
<212> TYPE: DNA
<213> ORGANISM: Artificial Sequence
<220> FEATURE:
<223> OTHER INFORMATION: XmaI-ATG-gamma-3-SpeI-F oligonucleotide

<400> SEQUENCE: 4

ccgggatgaa taatcaaaag attgttaacc tgaaagagaa ggtagcccag cttgaagcaa      60


<210> SEQ ID NO 5
```

-continued

<211> LENGTH: 60
<212> TYPE: DNA
<213> ORGANISM: Artificial Sequence
<220> FEATURE:
<223> OTHER INFORMATION: XmaI-ATG-gamma-3-SpeI-R oligonucleotide

<400> SEQUENCE: 5
ctagttgctt caagctgggc taccttctct ttcaggttaa caatcttttg attattcatc 60

<210> SEQ ID NO 6
<211> LENGTH: 60
<212> TYPE: DNA
<213> ORGANISM: Artificial Sequence
<220> FEATURE:
<223> OTHER INFORMATION: XmaI-ATG-2-gamma-3-SpeI-F oligonucleotide

<400> SEQUENCE: 6
ccgggatgaa taatcaaaag attgttaaca tcaaagagaa ggtagcccag atcgaagcaa 60

<210> SEQ ID NO 7
<211> LENGTH: 61
<212> TYPE: DNA
<213> ORGANISM: Artificial Sequence
<220> FEATURE:
<223> OTHER INFORMATION: XmaI-ATG-2-gamma-3-SpeI-R oligonucleotide

<400> SEQUENCE: 7
ctagtttgct tcgatctggg ctaccttctc tttgatgtta acaatctttt gattattcat 60
c 61

<210> SEQ ID NO 8
<211> LENGTH: 60
<212> TYPE: DNA
<213> ORGANISM: Artificial Sequence
<220> FEATURE:
<223> OTHER INFORMATION: XmaI-ATG-3-gamma-3-SpeI-F oligonucleotide

<400> SEQUENCE: 8
ccgggatgaa taatcaaaag cttgttaaca tcaaagagaa ggtagcccag atcgaagcaa 60

<210> SEQ ID NO 9
<211> LENGTH: 60
<212> TYPE: DNA
<213> ORGANISM: Artificial Sequence
<220> FEATURE:
<223> OTHER INFORMATION: XmaI-ATG-3-gamma-3-SpeI-R oligonucleotide

<400> SEQUENCE: 9
ctagttgctt cgatctgggc taccttctct ttgatgttaa caagcttttg attattcatc 60

<210> SEQ ID NO 10
<211> LENGTH: 42
<212> TYPE: DNA
<213> ORGANISM: Artificial Sequence
<220> FEATURE:
<223> OTHER INFORMATION: SpeI-(Ser4Gly)2-EcoRI-F oligonucleotide

<400> SEQUENCE: 10
actagttctt cttcttctgg ctcttcttct tctggcgaat tc 42

<210> SEQ ID NO 11
<211> LENGTH: 42
<212> TYPE: DNA
<213> ORGANISM: Artificial Sequence
<220> FEATURE:
<223> OTHER INFORMATION: SpeI-(Ser4Gly)2-EcoRI-R oligonucleotide

<400> SEQUENCE: 11
gaattcgcca gaagaagaag agccagaaga agaagaacta gt 42

<210> SEQ ID NO 12
<211> LENGTH: 24
<212> TYPE: DNA
<213> ORGANISM: Artificial Sequence
<220> FEATURE:
<223> OTHER INFORMATION: EcoRI-ASM-F oligonucleotide

<400> SEQUENCE: 12
aattcccccg ctacggagcg tcac 24

<210> SEQ ID NO 13
<211> LENGTH: 25
<212> TYPE: DNA
<213> ORGANISM: Artificial Sequence
<220> FEATURE:
<223> OTHER INFORMATION: ASM-XbaI-R oligonucleotide

<400> SEQUENCE: 13
ctagactagc aaaacagtgg ccttg 25

<210> SEQ ID NO 14
<211> LENGTH: 7
<212> TYPE: PRT
<213> ORGANISM: Artificial Sequence
<220> FEATURE:
<223> OTHER INFORMATION: phage display-derived peptide A1

<400> SEQUENCE: 14

Tyr Pro Ala Ser Tyr Gln Arg
1 5

<210> SEQ ID NO 15
<211> LENGTH: 7
<212> TYPE: PRT
<213> ORGANISM: Artificial Sequence
<220> FEATURE:
<223> OTHER INFORMATION: phage display-derived peptide B7

<400> SEQUENCE: 15

Tyr Gln Ala Thr Pro Leu Pro
1 5

<210> SEQ ID NO 16
<211> LENGTH: 7
<212> TYPE: PRT
<213> ORGANISM: Artificial Sequence
<220> FEATURE:
<223> OTHER INFORMATION: phage display-derived peptide B8

<400> SEQUENCE: 16

Gly Ser Leu Leu Ser Ala Ala
1 5

<210> SEQ ID NO 17
<211> LENGTH: 7
<212> TYPE: PRT
<213> ORGANISM: Artificial Sequence
<220> FEATURE:
<223> OTHER INFORMATION: phage display-derived peptide B9

<400> SEQUENCE: 17

Phe Ser Pro His Ser Arg Thr 1 5

<210> SEQ ID NO 18
<211> LENGTH: 7
<212> TYPE: PRT
<213> ORGANISM: Artificial Sequence
<220> FEATURE:
<223> OTHER INFORMATION: phage display-derived peptide B10

<400> SEQUENCE: 18

Tyr Pro Phe Leu Pro Thr Ala
1 5

<210> SEQ ID NO 19
<211> LENGTH: 7
<212> TYPE: PRT
<213> ORGANISM: Artificial Sequence
<220> FEATURE:
<223> OTHER INFORMATION: phage display-derived peptide D6

<400> SEQUENCE: 19

Gly Cys Lys Leu Cys Ala Gln
1 5

<210> SEQ ID NO 20
<211> LENGTH: 30
<212> TYPE: DNA
<213> ORGANISM: Artificial Sequence
<220> FEATURE:
<223> OTHER INFORMATION: XmaI-ATG-A1-SpeI-F oligonucleotide

<400> SEQUENCE: 20
ccgggatgta ccccgccagc taccagcgga 30

<210> SEQ ID NO 21
<211> LENGTH: 31
<212> TYPE: DNA
<213> ORGANISM: Artificial Sequence
<220> FEATURE:
<223> OTHER INFORMATION: XmaI-ATG-A1-SpeI-R oligonucleotide

<400> SEQUENCE: 21
ctagtccgct ggtagctggc ggggtacatc c 31

<210> SEQ ID NO 22
<211> LENGTH: 30
<212> TYPE: DNA
<213> ORGANISM: Artificial Sequence
<220> FEATURE:
<223> OTHER INFORMATION: XmaI-ATG-D6-SpeI-F oligonucleotide

<400> SEQUENCE: 22
ccgggatggg ctgcaagctg tgcgcccaga 30

<210> SEQ ID NO 23
<211> LENGTH: 30
<212> TYPE: DNA
<213> ORGANISM: Artificial Sequence
<220> FEATURE:
<223> OTHER INFORMATION: XmaI-ATG-D6-SpeI-R oligonucleotide

<400> SEQUENCE: 23
ctagtctggg cgcacagctt gcagcccatc 30

<210> SEQ ID NO 24
<211> LENGTH: 30

-continued

<212> TYPE: DNA
<213> ORGANISM: Artificial Sequence
<220> FEATURE:
<223> OTHER INFORMATION: XmaI-ATG-B7-SpeI-F oligonucleotide

<400> SEQUENCE: 24
ccgggatgta ccaggccacc cccctgccca 30

<210> SEQ ID NO 25
<211> LENGTH: 30
<212> TYPE: DNA
<213> ORGANISM: Artificial Sequence
<220> FEATURE:
<223> OTHER INFORMATION: XmaI-ATG-B7-SpeI-R oligonucleotide

<400> SEQUENCE: 25
ctagtgggca gggggtggc ctggtacatc 30

<210> SEQ ID NO 26
<211> LENGTH: 30
<212> TYPE: DNA
<213> ORGANISM: Artificial Sequence
<220> FEATURE:
<223> OTHER INFORMATION: XmaI-ATG-B8-SpeI-F oligonucleotide

<400> SEQUENCE: 26
ccgggatggg cagcctgctg agcgccgcca 30

<210> SEQ ID NO 27
<211> LENGTH: 30
<212> TYPE: DNA
<213> ORGANISM: Artificial Sequence
<220> FEATURE:
<223> OTHER INFORMATION: XmaI-ATG-B8-SpeI-R oligonucleotide

<400> SEQUENCE: 27
ctagtggcgg cgctcagcag gctgcccatc 30

<210> SEQ ID NO 28
<211> LENGTH: 30
<212> TYPE: DNA
<213> ORGANISM: Artificial Sequence
<220> FEATURE:
<223> OTHER INFORMATION: XmaI-ATG-B9-SpeI-F oligonucleotide

<400> SEQUENCE: 28
ccgggatgtt cagcccccac agccggacca 30

<210> SEQ ID NO 29
<211> LENGTH: 30
<212> TYPE: DNA
<213> ORGANISM: Artificial Sequence
<220> FEATURE:
<223> OTHER INFORMATION: XmaI-ATG-B9-SpeI-R oligonucleotide

<400> SEQUENCE: 29
ctagtggtcc ggctgtgggg gctgaacatc 30

<210> SEQ ID NO 30
<211> LENGTH: 30
<212> TYPE: DNA
<213> ORGANISM: Artificial Sequence
<220> FEATURE:
<223> OTHER INFORMATION: XmaI-ATG-B10-SpeI-F oligonucleotide

<400> SEQUENCE: 30

-continued

```
ccgggatgta ccccttcctg cccaccgcca                                        30


<210> SEQ ID NO 31
<211> LENGTH: 30
<212> TYPE: DNA
<213> ORGANISM: Artificial Sequence
<220> FEATURE:
<223> OTHER INFORMATION: XmaI-ATG-B10-SpeI-R oligonucleotide

<400> SEQUENCE: 31

ctagtggcgg tgggcaggaa ggggtacatc                                        30
```

PEPTIDES FOR TRANSPORT OF THERAPEUTICS AND THEIR CARRIERS IN MOUSE MODELS AND HUMANS

CROSS-REFERENCE TO RELATED APPLICATIONS

This application is a U.S. national phase application under the provisions of 35 U.S.C. §371 of International Patent Application No. PCT/US2010/037490 filed Jun. 4, 2010, which in turn claims the benefit of priority of U.S. Provisional Patent Application No. 61/184,657 filed Jun. 5, 2009 in the names of Silvia Muro Galindo and Carmen Garnacho Montero for "FIBRINOGEN-DERIVED PEPTIDES FOR TRANSPORT OF THERAPEUTICS AND THEIR CARRIERS IN MOUSE MODELS AND HUMANS" and further claims the benefit of U.S. Provisional Patent Application No. 61/220,404 filed Jun. 25, 2009, in the names of Silvia Muro Galindo, Ming Meng, and Carmen Garnacho Montero for "PEPTIDES FOR TRANSPORT OF THERAPEUTICS AND THEIR CARRIERS IN MOUSE MODELS AND HUMANS." The disclosures of such international patent application and U.S. Provisional Patent Application Nos. 61/184,657 and 61/220,404 are hereby incorporated herein by reference in their respective entireties, for all purposes.

GOVERNMENT RIGHTS IN THE INVENTION

This invention was made with government support under Grant Nos. R21 HL85533 and P30 DK47757, awarded by the National Institutes of Health (NIH). The government has certain rights in this invention.

FIELD OF THE INVENTION

The present invention relates to novel ICAM-1-targeting peptides and methods of using the same in compositions for targeted delivery and transport of agents for research, analytical, diagnostic or therapeutic purposes.

DESCRIPTION OF THE RELATED ART

Site-specific delivery of therapeutic compounds, as well as imaging and diagnostic agents, to sites of pathology is an important goal that would permit optimization of the efficiency of such agents and minimization of their potential toxicity. However, most therapeutic and diagnostic agents do not present intrinsic affinity to any particular organ, tissue, cell type, or sub-cellular compartment within the body, which results in rapid clearance, inefficient transport to the target sites, and suboptimal effects. This obstacle can be surmounted by coupling the compounds to be delivered to targeting carriers (including natural ligands, antibodies, affinity peptides, aptamers, sugar residues, nanoparticles, and other drug delivery systems) that recognize determinants expressed by cells at the sites where the intervention is required. Targeting of such carriers to cell surface molecules involved in endocytic vesicular transport helps improve delivery of therapeutic and diagnostic agents both intracellularly (e.g, to the cytosol, vesicular compartments such as lysosomes, the nucleus, etc.) and across cell layers for penetration into a given tissue (e.g., from the circulation into the lungs and/or the central nervous system).

In this context, the vascular route is a standard and convenient path for targeted delivery of therapeutics and diagnostic agents, since endothelial cells: (i) represent important targets for clinical interventions in a plethora of pathologies, including, but not restricted to, diseases with strong pulmonary and cardiovascular components; and (ii) control the transport of substances between the bloodstream and the surrounding tissue, a function particularly relevant in the case of tight endothelial barriers such as those located at the lung and, primarily, the central nervous system (CNS). In addition to transport from the bloodstream into tissues, or when other routes of administration are used (e.g., intratracheal, intranasal, intraperitoneal, intracerebral, intrathecal, oral, rectal, etc.), targeting to cells into a given tissue and subsequent transport into or across those cells, also requires identification of target molecules present on those areas.

Significant progress in the identification of such target molecules or cellular surface determinants, both relatively selective for certain cell types and more general molecules characteristic of several or many cell types in the body, has been achieved using techniques including phage display libraries and monoclonal antibodies. However, the utility of most of these newly identified candidate determinants for drug delivery in humans remains to be tested. For example, functions of most cell surface determinants defined by these modern techniques are either not known or are responsible for vital physiological processes in the body, hence inadvertent intervention into or blocking of their functions may lead to harmful side effects.

Furthermore, most objects including therapeutics and their carriers targeted to cells using these determinants, either remain on the cell surface in all instances, or they are always internalized upon targeting, which does not provide the opportunity to use the same targeting strategy for transport and delivery to these two different environments, internal and external to the cell. For those determinants leading to internalization, this occurs either via passive or receptor-mediated endocytosis, e.g., via natural clathrin-mediated and caveolar-mediated pathways, macropinocytosis or phagocytosis. Some of these natural pathways, e.g., macropinocytosis and phagocytosis, are typically associated to cells of the immune system, precluding targeting and delivery to other cell types in the body. (Muro S., et al. *Curr. Vasc. Pharmacol.* 2004; 2:281-99.) In addition, all these pathways are often suppressed in many types of human pathology including inflammation, metabolic disorders, ischemia and abnormalities of blood flow, negatively impacting delivery in the setting in which drugs are needed in the tissues.

Also, intracellular and transcellular transporting capacity of clathrin-mediated and caveolar-mediated pathways common to most cell types in the body (e.g., exploited by targeting to manose-6-phosphate receptor, glucose receptors, LDL-family receptors, receptor associated protein RAP, insulin-like growth factor II, transferrin, insulin, folate receptor, and other receptors), is restricted to relatively small objects, typically <100 nm in diameter. (Muro S., et al., *Curr. Vasc. Pharmacol.* 2004; 2:281-99; Pardridge W. M., et al., *Curr. Opin. Pharmacol.* 2006; 6:494-500; Schnitzer J. E., et al., *Adv. Drug Deliv. Rev.* 2001; 49:265-80) For instance, phage particles (~800 nm length) targeted to pulmonary caveolar determinants simply do not bind to their intended targets due to inaccessibility of caveolar determinants for objects larger than 50-80 nm, from the circulation. This fact highly restricts transport of many emerging targeted drug and diagnostic delivery systems (100 nm-1 μm) with promising applications in virtue of their high affinity and payload.

Finally, even if these obstacles of selection of a proper target determinant are overcome, safe and effective targeting in the body of therapeutic and diagnostic agents, and/or their carriers, requires adequate targeting molecules with high affinity, e.g., to be able to withstand dragging forces of the shear stress in the circulation, yet relatively "invisible" and innocuous to the body to avoid secondary detrimental reactions to these molecules, particularly if recurrent administrations are necessary for an effective treatment.

ICAM-1 is an Ig-like transmembrane glycoprotein expressed at the luminal surface of many cell types, including primarily endothelial cells in the blood vessels, and also white blood cells, epithelial cells, neurons and glial cells, muscle cells, and others. It is constitutively expressed and its expression is upregulated by many pathological mediators, including thrombin, fibrinogen/fibrin, cytokines (IL-1, IL-6, IFNγ and TNF-α), lipopolysaccharide, hypoxia, reactive oxygen species, and biomechanical forces and acute changes in shear stress that cause rapid cytoskeletal reorganization.

ICAM-1 is involved in adhesion to cells of leukocytes and fibrinogen/fibrin, apoptotic cells, necrotic cells, and metastatic cells, and also certain pathogens and pathogen infected cells can bind to ICAM-1, including major-class human Rhinovirus, coxsackievirus A, respiratory syncytial virus, poliovirus, nontypeable *Haemophilus influenzae*, HIV and HIV-infected leukocytes, sickle cells and red blood cells infected with *Plasmodium falciparum*, and some bacteria.

Binding of leukocytes, fibrinogen/fibrin, pathogens, and infected cells to ICAM-1 leads to induction of a series of regulatory events, including generation of reactive oxygen species (ROS) such as via activation of NAPDH oxidase, cytoskeleton remodeling and adherence such as those involving actin, tubulin, ERMs, Rho, ROCK, FAK, paxillin, cell signaling such as that involved in antigen presentation events in immune cells, or those that occur via certain Src kinases, PKC, PI3K, PLC, ERK, MAPK, JNK, and regulation of gene expression such as that of genes involved in cell survival, cell growth, ROS production, cytokine production, expression or surface molecules, and cytoskeletal rearrangements.

Despite being involved in adhesion or binding of various materials, including proteins, cells, and pathogens, ICAM-1 is not an endocytic receptor. (Muro S., VCAM-1 and ICAM-1. In: Aird W C, ed. *Endothelial Biomedicine*: Cambridge University Press.; 2007: 1058-70; Rothlein R. et al., *J. Immunol.* 1986; 137:1270-4.) Indeed, cells expressing ICAM-1 do not internalize their natural ligands, leukocytes and fibrinogen or fibrin and some pathogens. Similarly, cells do not internalize anti-ICAM antibodies, which remain adhered to the cell surface upon binding to ICAM-1, a strategy which can be used to target and deliver therapeutic and imaging agents to the cell surface. (Murciano J. C., et al., *Blood* 2003; 101: 3977-84; Muro S., et al., *J. Cell Sci.* 2003; 116:1599-609.) However, paradoxically cells actively internalize model multivalent ligands and ICAM-1-targeted drug delivery vehicles, such as anti-ICAM conjugates prepared by crosslinking biotinylated antibodies via streptavidin, latex beads and biodegradable polymer nanocarriers coated with anti-ICAM. (Muro S., et al., *J. Cell Sci.* 2003; 116:1599-609; Muro S. et al., *Am. J. Physiol. Cell Physiol.* 2003; 285:C1339-47; Muro S., et al., *Blood* 2005; 105:650-8; Muro S., et al., *Mol. Ther.* 2008; 16:1450-8; Muro S. et al., *Am. J. Physiol. Lung Cell Mol. Physiol.* 2006; 290:L809-17; Muro S. et al., *Mol. Ther.* 2006; 13:135-41.)

Both the cellular and molecular mechanisms of initiation and execution of this internalization pathway induced by anchored anti-ICAM conjugates and carriers themselves (known to as Cell Adhesion Molecule- or CAM-mediated endocytosis), as well as the kinetics and mechanisms of the subsequent intracellular or transcellular trafficking of the internalized materials, are distinct from natural endocytic mechanisms (typically used for drug delivery strategies), including clathrin-coated pits, caveolar-mediated endocytosis, phagocytosis or macropinocytosis. (Muro S., et al., *J. Cell Sci.* 2003; 116:1599-609; Muro S. et al., *Am. J. Physiol. Cell Physiol.* 2003; 285:C1339-47; Muro S., et al., *Blood* 2005; 105:650-8; Muro S., et al., *Mol. Ther.* 2008; 16:1450-8; Muro S. et al., *Am. J. Physiol. Lung Cell Mol. Physiol.* 2006; 290: L809-17; Muro S, et al., *J. Pharmacol. Exp. Ther.* 2006; 317:1161-9.) This mechanism of uptake by cells is highly permissive for internalization of objects with a variety of sizes and shapes, and it has been used to deliver therapeutic and imaging agents intracellularly, by multivalent anti-ICAM carriers. Furthermore, both anti-ICAM and anti-ICAM conjugates and carriers efficiently target organs upon intravenous injection in laboratory animals, efficiently delivering therapeutic agents and diagnostic probes in a safe manner. Blockage of ICAM-1 adhesive function provides side benefits, e.g., anti-inflammatory effects.

However, the use of targeting antibodies in a clinical context has clear limitations such as high immunogenicity. Immunoglobulins or IgGs containing Fc can prompt the formation of immunocomplexes that bind to Fc and/or complement receptors on the surface of antigen presenting cells, also leading to activation of T lymphocytes and generation of long lasting immunity. Targeting vectors derived from anti-ICAM represent interesting substitutes, for instance, IgG-derived fragments containing variable regions, such as divalent F(ab')2 or monovalent Fab fragments can be produced by enzymatic cleavage of intact IgG molecules. Alternatively, single chain Fv constructs (scFv) are easily generated from the sequences corresponding to the variable regions of the genes encoding the antibody heavy and light chains. Both sequences are then fused through a flexible linker that allows the construct to fold into a molecular architecture capable of recognizing the antigen with high fidelity. Apart from exerting a lower immunogenicity, scFv constructs present additional advantages over intact antibodies and their fragments. They can be easily expressed in prokaryotic and insect cell systems facilitating bulk synthesis while retaining recognition ability, they can be designed to form bivalent or multivalent forms with enhanced affinity, and they can be directly produced as a fusion protein containing the therapeutic cargo of interest. In particular, scFv constructs and humanized antibodies have been successfully generated from several anti-ICAM forms and provide efficient targeting to ICAM-1 in gene delivery and anti-inflammatory settings.

Despite these advantages of antibody-derived targeting molecules their efficiency:safety ratio is not optimal and these entities to be administered in a patient are not naturally present in the body and are likely to result in recognition by the clearance systems. This is also impacted by the still "large" size of these protein entities, for instance, scFv fragments are typically in a ~20-30 kDa size range, which contain many epitopes that can be recognized by the immune system. Also, good specific antibodies and their derivatives typically recognize only antigens from single species, precluding the use of the same designs both in animal testing and subsequent human trials.

An alternative to antibody-based systems are peptides capable of binding to ICAM-1. Several ICAM-1 affinity peptides have been generated from phage libraries or designed from ICAM-1 interacting molecules, such as LFA-1 integrin of leukocytes. (Hayashi T., et al., *Digestion* 2001; 63 Suppl 1:87-92; Jaafari M. R., et al., *Drug Deliv.* 2002; 9:1-9; Sillerud L. O., et al, *J. Pept. Res.* 2004; 64:127-40; Smith J. D., et al, Proc. Natl. Acad. Sci. USA 2000; 97:1766-71; Springer A. L., et al., *Mol. Biochem. Parasitol.* 2004; 137:55-64; Welply J. K., et al., *Proteins* 1996; 26:262-70; Xu C. R., et al., *J. Biomol. Struct. Dyn.* 2002; 19:789-99; Belizaire A. K., et al.,

*Biochem. Biophys. Res. Commun.* 2003; 309:625-30; Chittasupho C., et al., *Eur. J. Pharm. Sci.* 2009; 37:141-50; Kam J. L., et al., *Cancer Res.* 1998; 58:5577-81; Anderson M. E., et al., *Pharm. Res.* 2003; 20:1523-32.) This is the case for a battery of 16-mer peptides identified by phage display by Alankov's group, (Belizaire A. K., et al., *Biochem. Biophys. Res. Commun.* 2003; 309:625-30) however these peptides were tested to block ICAM-1 stimulation during antigen presentation in immune cells, but not targeting of therapeutics or carriers, they were designed to bind to mouse ICAM-1 but not human ICAM-1, and they do not represent natural molecules present in the body. On the other hand, Hugh's group designed a synthetic peptide derived from MUC151, a mucin-family membrane glycoprotein overexpressed on the surface of cancer cells and other cells, which binds to ICAM-1, yet this peptide was only tested for inhibition of mucin interaction with ICAM-1, but not targeting of drugs or carriers, and only a peptide that was 120-mer long, but not shorter derivates, was efficient in binding to ICAM-1, hence, the large size of this peptide may preclude from certain applications, e.g., design of stable chimeric proteins containing this targeting moiety. Another example of an ICAM-1 binding peptide is that of cLABL, a short cyclic peptide derived from LFA-1 which has been used to target therapeutic carriers to ICAM-1. (Chittasupho C., et al., *Eur. J. Pharm. Sci.* 2009; 37:141-50; Kam J. L., et al., *Cancer Res.* 1998; 58:5577-81; Anderson M. E., et al., *Pharm. Res.* 2003; 20:1523-32.) However, this peptide has been designed to recognize only human ICAM-1, its efficacy in targeting carriers in vivo has not been tested, and it is likely to elicit detrimental responses that natural LFA-1 elicits in cells, e.g., pathological activation in endothelium signaling during inflammation.

There therefore remains a need in the art for the development of targeting moieties for site-specific delivery of therapeutic and diagnostic agents allowing for safe, effective, efficient and specific binding to a target and/or subsequent transport into and/or across cells. The present invention provides such targeting carriers and methods of using the same.

SUMMARY OF THE INVENTION

This invention relates to the use of targeting moieties effective as targeting molecules providing efficient and specific binding of therapeutic agents and drug delivery systems to a determinant present in both mice and humans, e.g. for delivery to the surface of a cell and/or effective and safe transport into and/or across cells. In one aspect the targeting moieties are short peptides derived from fibrinogen, a natural protein present in the human circulation. In a further aspect, the targeting moieties are a set of peptides identified by phage display.

The present invention relates to a delivery composition for delivery of an agent to a cell, tissue or organ, comprising: a) a targeting moiety comprising a peptide or protein selected from γ3, derivatives of γ3, A1, B7, B8, B9, B10, and D6; and b) an agent, wherein the targeting moiety recognizes and binds to a target on a cell, tissue or organ, and is effective to deliver the agent to the cell, tissue or organ.

In one aspect, the invention relates to a method for delivering an agent to a cell, tissue or organ, comprising administration of a delivery composition comprising: a) a targeting moiety comprising a peptide or protein selected from γ3, derivatives of γ3 (e.g., 2γ3 and 3γ3), A1, B7, B8, B9, B10, and D6; and b) an agent, wherein the targeting moiety recognizes and binds to a target on a cell, tissue or organ, and is effective to deliver the agent to the cell, tissue or organ.

In another aspect, the invention relates to a method of treating a disorder involving ICAM-1 or involving a pathway including ICAM-1 function or a symptom of such disorder, comprising administration of a delivery composition comprising: a) a targeting moiety comprising a peptide or protein selected from γ3, derivatives of γ3, A1, B7, B8, B9, B10, and D6; and b) an agent, wherein the targeting moiety recognizes and binds to a target on a cell, tissue or organ, and is effective to deliver the agent to the cell, tissue or organ.

In a further aspect the invention relates to a method of inhibiting inflammation in a subject comprising administration of a delivery composition to the subject, the delivery composition comprising: a) a targeting moiety comprising a peptide or protein selected from γ3, derivatives of γ3, A1, B7, B8, B9, B10, and D6; and, optionally, b) an agent, wherein the targeting moiety recognizes and binds to a target on a cell, tissue or organ, and is effective to deliver the agent to the cell, tissue or organ and wherein the composition is further effective to inhibit leukocyte transmigration across an ICAM-1-containing cell.

In a still further aspect the invention relates to a method of reducing vascular lodging of a thombus in a subject comprising administration of a delivery composition to the subject, the delivery composition comprising: a) a targeting moiety comprising a peptide or protein selected from γ3, derivatives of γ3, A1, B7, B8, B9, B10, and D6; and, optionally, b) an agent, wherein the targeting moiety recognizes and binds to a target on a cell, tissue or organ, and is effective to deliver the agent to the cell, tissue or organ.

In yet another aspect, the invention relates to a kit comprising instructional material and the delivery composition, in which the delivery composition includes: a) a targeting moiety comprising a peptide or protein selected from γ3, derivatives of γ3, A1, B7, B8, B9, B10, and D6; and b) an agent, wherein the targeting moiety recognizes and binds to a target on a cell, tissue or organ, and is effective to deliver the agent to the cell, tissue or organ.

A further aspect of the invention relates to a targeting moiety selected from SEQ ID NO: 1, SEQ ID NO: 2, SEQ ID NO: 3, SEQ ID NO: 14, SEQ ID NO: 15, SEQ ID NO: 16, SEQ ID NO: 17, SEQ ID NO: 18, and SEQ ID NO: 19.

Another aspect of the invention relates to the ICAM-1-targeting ASM plasmid (B) comprising a nucleic acid sequence encoding any of γ3, derivatives of γ3, A1, B7, B8, B9, B10, and D6.

In yet another aspect the invention relates to a nucleic acid sequence encoding a targeting moiety selected from γ3, derivatives of γ3 (e.g., 2γ3 and 3γ3), A1, B7, B8, B9, B10, and D6. In a further aspect the invention relates to a delivery composition comprising a nucleic acid sequence encoding a targeting moiety selected from γ3, derivatives of γ3, A1, B7, B8, B9, B10, and D6.

In a still further aspect the invention relates to a delivery composition for delivery of an agent to a cell, comprising: a) a nucleic acid sequence encoding a targeting moiety selected from γ3, derivatives of γ3, A1, B7, B8, B9, B10, and D6; and b) a second nucleic acid sequence encoding an agent, wherein, upon expression, the targeting moiety recognizes and binds to a target on a cell, tissue or organ, and is effective to deliver the agent to the cell, tissue or organ. In yet another aspect the invention relates to a method for delivering an agent to a cell, tissue or organ comprising administration of such a delivery composition. Still another aspect of the invention relates to a method of treating a disorder involving ICAM-1 or involving a pathway including ICAM-1 function or a symptom of such disorder, comprising administration of such a delivery composition.

In a further aspect the invention relates to a method of inhibiting inflammation in a subject comprising administration of a delivery composition to the subject, the delivery composition comprising: a) a nucleic acid sequence encoding a targeting moiety selected from γ3, derivatives of γ3, A1, B7, B8, B9, B10, and D6; and, optionally, b) a second nucleic acid sequence encoding an agent, wherein, upon expression, the targeting moiety recognizes and binds to a target on a cell, tissue or organ, and is effective to deliver the agent to the cell, tissue or organ and wherein the composition is further effective to inhibit leukocyte transmigration across an ICAM-1-containing cell.

In a still further aspect the invention relates to a method of reducing vascular lodging in a subject comprising administration of a delivery composition to the subject, the delivery composition comprising: a) a nucleic acid sequence encoding a targeting moiety selected from γ3, derivatives of γ3, A1, B7, B8, B9, B10, and D6; and, optionally, b) a second nucleic acid sequence encoding an agent, wherein, upon expression, the targeting moiety recognizes and binds to a target on a cell, tissue or organ, and is effective to deliver the agent to the cell, tissue or organ.

Other aspects, features and embodiments of the invention will be more fully apparent from the ensuing disclosure and appended claims.

BRIEF DESCRIPTION OF THE DRAWINGS

FIG. 2D is a graph of location of the carriers, as a function of their size.

FIG. 4B provides a graph demonstrating the effects of blocking ICAM-1 or other molecules on the binding of γ3 carriers with ASM cargo and binding to cells that do not express ICAM-1; FIGS. 4C-E provide graphs of the lysosomal transport as a function of time, peptide type (γ3, 2γ3 and 3γ3) and various inhibitions and activations.

DETAILED DESCRIPTION OF THE INVENTION AND PREFERRED EMBODIMENTS THEREOF

Figure 1:
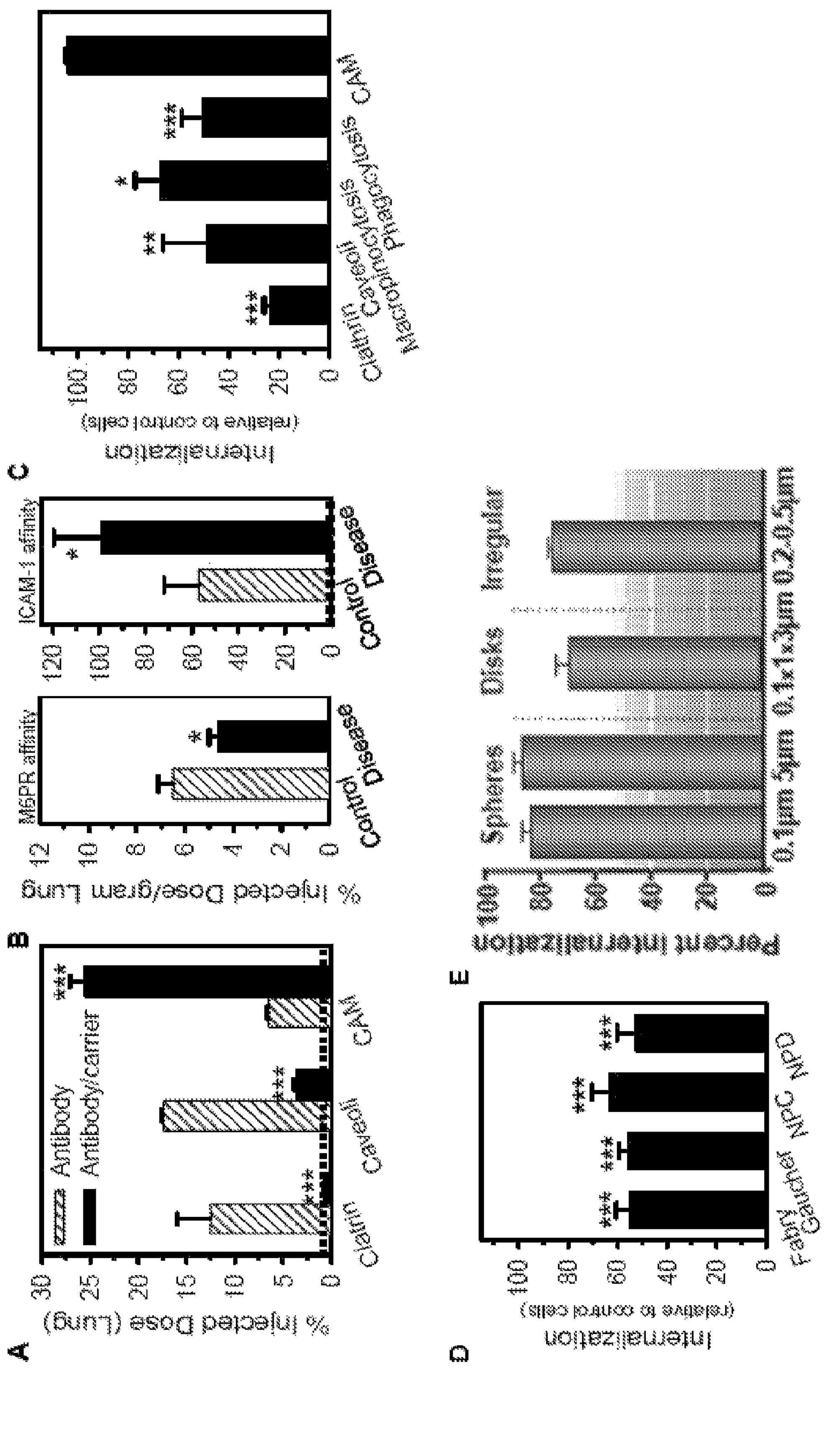
FIG. 1 illustrates the results of Example 1, comparing the in vivo accessibility and internalization in cells, of free anti-ICAM and anti-ICAM carriers, in vivo and in cell cultures, in normal and disease conditions, via ICAM-1 and CAM-mediated endocytosis, as compared to endocytosis mediated by clathrin, caveoli, macropinocytosis and phagocytosis.

The present invention relates to targeting moieties used to provide more effective, versatile, and safe targeting and transport of molecular probes, diagnostic and therapeutic agents and/or their carriers. The moieties provided are useful in both research settings and in the context of translational science and clinical interventions. The invention further relates to compositions containing such targeting moieties and to methods of using such target moieties.

"Targeting moiety" as used herein refers to moieties useful in the compositions and methods described herein, wherein the moieties specifically target a surface expressed protein, e.g., ICAM-1. In one embodiment the targeting moieties mediate efficient and specific delivery of an agent to a determinant through such targeting. Targeting moieties and/or their carriers may be varied, such as by size, shape, and/or valency in order to modulate delivery. A targeting moiety may also be described herein as any of an "affinity moiety," an "affinity peptide," a "targeting peptide," "targeting molecule," or "ligand."

"Carrier" as used herein refers to an accessory substance present as a vehicle during the transfer of an active substance to a target. In one embodiment, the targeting moieties are carriers for the agents. As such, the targeting moieties may also be referred to herein as "targeting carriers." In another embodiment, "delivery carriers" are provided for transfer or delivery of a composition containing the targeting moiety and/or the agent to the target.

"Agent" as used herein refers to the subject of the targeting or transport of the targeting moiety. In conjunction with the action of the targeting moiety, agents may be transported to a cell, to the surface of a cell, into a cell or across a cell. Specifically, the targeting moiety provides a means for transporting agents such as, but not limited to, molecular probes, diagnostic and therapeutic agents, biologically active agents, research agents, analytical agents, imaging agents, monitoring agents, enzymes, proteins, peptides, nucleic acids, lipids, sugars, hormones, lipoproteins, chemicals, viruses, bacteria, and cells. An agent may also be described herein as a "cargo."

"Target" as used herein refers to a determinant recognized by the targeting moiety. In one embodiment a target recognized by this targeting moiety is a molecule expressed on the surface of a cell which constitutes a part of the first layer after administration within a tissue. Such cells are therefore easily accessible. Examples of such cells include, but are not limited to, endothelial cells in the context of preferable intravascular (intravenous or intra-arterial) administration; epithelial cells in the case of gastrointestinal, nasal, intratracheal, or rectal administration; immune system cells for treatment of conditions affecting these cells; muscle cells for intramuscular administration; glial cells and neurons for intra-cerebral or intrathecal administration and the like. Expression of the target molecule in normal physiological conditions would provide a target for protective or prophylactic interventions, whereas up-regulation of the expression of the molecule in many pathologies would provide a target for site-specific delivery of therapeutic and diagnostic agents to disease sites. In another embodiment a target recognized by the targeting moiety may be a tissue or an organ. A target may also be described herein as a "target molecule," a "determinant," or a "receptor."

Where the target molecule is expressed on the surface of a cell, it should be stably expressed on the cell surface to allow sufficient time frame for targeted interventions. If the cell surface is the intended destination for an agent, the target molecule should remain on the cell surface. If the interior of the cell is the intended destination for an agent, the target molecule should provide internalization within the cell body or safe transport across cellular layers (e.g., by an endocytic pathway or transcytosis, respectively) upon proper induction by targeting. Such internalization may be used for intracellular delivery of agents to the cell interior or transcellular delivery for penetration across cell layers or tissues.

The physiological function of the target molecule is not detrimental (and, preferably is beneficial) to the interaction of the agent with the target molecule and/or the biological, physiological, or pathological function of the target molecule. The mechanism associated with interaction of the agent and the target molecules resulting in any of surface residency, intracellular transport or transcellular transport should be not affected by disease, and the parameters of such interaction should be known, to allow rational design of strategies for delivery of therapeutic and/or diagnostic agents with precision.

In one embodiment the invention provides a composition including a targeting moiety, where the targeting moiety recognizes and binds to a target on a cell. Optionally, the composition may further comprise a delivery carrier. In another embodiment the composition includes a nucleic acid encoding a targeting moiety, where the targeting moiety, when expressed, recognizes and binds to a target on a cell.

In still another embodiment the invention provides a composition for delivery of an agent to a cell, where the delivery composition includes both a targeting moiety and one or more agents, where the targeting moiety recognizes and binds to a target on a cell and is effective to deliver the agent to the cell. Optionally, the composition may further comprise a delivery carrier. In a further embodiment, the invention provides a composition for delivery of an agent to a cell, where the delivery composition includes both a nucleic acid encoding a targeting moiety and a nucleic acid encoding an agent, where the targeting moiety, when expressed, recognizes and binds to a target on a cell and is effective to deliver the agent to the cell. Expression of the agent may be co-expression with the targeting moiety or may be separately expressed.

Expression and production systems as described above may include, but are not limited to, viruses, bacteria, and eukaryotic cells expressing and producing the targeting moieties and/or the agents.

In an exemplary embodiment, the inventors explored the utility as a targeting moiety of a 17 amino acid peptide derived from the γ chain of fibrinogen and its cleavage product fibrin, known as γ3, (Altieri D. C., et al., *J. Biol. Chem.* 1995; 270:696-9; D'Souza S. E., et al., *J. Biol. Chem.* 1996; 271: 24270-7; Duperray A., et al., *J. Biol. Chem.* 1997; 272:435-41; Languino, L. R., et al., *Cell* 1993; 73:1423-34.) and two peptides derived from γ3, derivatives termed 2γ3 and 3γ3. Fibrinogen is a dimer of three pairs of disulfide-bonded chains (Aα, Bβ, and γ) arranged in three globular domains (a central E domain and two peripheral D domains). (Weisel J. W., *Adv. Protein Chem.* 2005; 70:247-99.) Cleavage by thrombin of fibrinopeptides A and B from the amino-terminus of chains Aα and Bβ, converts fibrinogen into fibrin and exposes polymerization sites for forming fibrin mesh, typically involved in blood clotting. Both fibrinogen and fibrin form a molecular bridge between endothelial ICAM-1 and leukocyte β2 integrin Mac-1, which is the main function attributed to ICAM-1 in regard to fibrinogen/fibrin interaction: strengthening of the adhesion between these two cell types during inflammation.

Although the γ3 sequence within the fibrinogen/fibrin γ chain has been demonstrated to bind to human ICAM-1, none of native fibrinogen, fibrin, the γ chain, or the γ3 peptide had been coupled to or tested in the context of targeting therapeutic or diagnostic agents or their carriers to ICAM-1, or any other cell surface determinant, prior to the present invention. In addition, they had not been observed to affect cellular transport, for example internalization by cells by induction of CAM-mediated endocytosis or by any other method, and the potential recognition of ICAM-1 in other species (e.g., mouse) by the γ3 peptide was unknown. Prior to the inventors' work, potential use of γ3 for safe and efficient ICAM-1 targeting and delivery of therapeutic and diagnostic compounds, and their carriers, was unpredictable and unlikely.

γ3, 2γ3 and 3γ3 were examined as targeting moieties with regard to targeting therapeutic agents to the surface molecule "intercellular adhesion molecule 1" (ICAM-1). Therefore, in one embodiment of the invention, the targeting moiety is selected from γ3 (amino-terminus NNQKIVNLKEKVAQLEA carboxyl-terminus (SEQ ID NO: 1)), 2γ3 (amino-terminus NNQKIVNIKEKVAQIEA carboxyl-terminus (SEQ ID NO: 2)), and 3γ3 (amino-terminus NNQKLVNIKEKVAQIEA carboxyl-terminus (SEQ ID NO: 3)), short peptides derived from fibrinogen, a natural protein present in human circulation, which retain their affinity and selectivity for particular target determinants, particularly ICAM-1.

As can be seen from SEQ ID NOs: 2 and 3, peptides 2γ3 and 3γ3 are derivatives of γ3. Peptides 2γ3 and 3γ3 both retain the affinity and selectivity for ICAM-1, as demonstrated by γ3. In another embodiment of the invention, the targeting moiety is an additional variant or derivative of γ3, wherein the variant or derivative is truncated or extended with respect to SEQ ID NO: 1 and/or contains one or more amino acid substitutions, deletions, insertions, and/or additions relative to SEQ ID NO: 1. Such a targeting moiety retains affinity and selectivity for particular target determinants, such as ICAM-1. Accordingly, targeting moieties as described herein may include peptidomimetics of any of γ3, 2γ3, or 3γ3 their nucleotide encoding sequences, and the viral, bacterial, or cellular systems expressing and/or producing these peptides.

In a further embodiment, the inventors explored the utility as a targeting moiety of various very short chain peptides developed utilizing phage display. From such investigation a battery of 7 amino acid peptides (termed A1, B7, B8, B9, B10 and D6) was determined to be individually useful as targeting moieties in targeting of ICAM-1. Therefore, in one embodiment of the invention, the targeting moiety is selected from A1 (amino-terminus YPASYQR carboxyl-terminus (SEQ ID NO: 14)), B7 (amino-terminus YQATPLP carboxyl-terminus (SEQ ID NO: 15)), B8 (amino-terminus GSLLSAA carboxyl-terminus (SEQ ID NO: 16)), B9 (amino-terminus FSPHSRT carboxyl-terminus (SEQ ID NO: 17)), B10 (amino-terminus YPFLPTA carboxyl-terminus (SEQ ID NO: 18)), D6 (amino-terminus GCKLCAQ carboxyl-terminus (SEQ ID NO: 19)), phage display-derived peptides. In another embodiment, the targeting moiety is an additional variant or derivative of any of A1, B7, B8, B9, B10 and D6, wherein the variant or derivative is truncated or extended with respect to any of SEQ ID NO: 14-19 and/or contains one or more amino acid substitutions, deletions, insertions, and/or additions relative to any of SEQ ID NO: 14-19. Such a targeting moiety retains affinity and selectivity for particular target determinants, such as ICAM-1. Accordingly, targeting moieties as described herein may include peptidomimetics of any of A1, B7, B8, B9, B10 and D6 their nucleotide encoding sequences, and the viral, bacterial, or cellular systems expressing and/or producing these peptides.

Phage-display technology was utilized to identify small 7-mer random sequence peptides capable of recognizing ICAM-1. Although this technique has been proven in the past regarding identification of peptides with recognition properties, classically phage-display of larger random peptide sequences is used, (e.g., >12 amino acids) to increase chances of specific recognition of a determinant. Importantly, although targeting peptides can be generated by this method, whether these peptides have the ability to induce (upon binding to their surface determinants) cellular signals to induce transport into and/or across cells is totally unpredictable. The importance of this is demonstrated in a recent publication by the present inventors (Garnacho et al., 2008, Journal of Controlled Release, 130:226-233), which indicates that binding of targeting moieties to different epitopes or regions of the same determinant may lead to surface retention of drug carriers, their endocytic transport, and/or differential intracellular destination, even when the targeted epitopes are in close proximity or even overlapping. Moreover, some targeting moieties do not bind to their targets after coupling them to carriers (Garnacho et al., 2008, Journal of Controlled Release, 130:226-233).

Targeting moieties that are proteins or peptides may be obtained by any method known to those of skill in the art. Specifically, such proteins or peptides may be synthetic or recombinant or may be isolated from a naturally-occurring source or may be identified by phage display. Isolation of proteins or peptides of the invention so identified may be performed by any known method, including use of oligonucleotides, such as those described in Example 8 below.

In one embodiment, the targeting moiety is a protein or peptide expressed from a polynucleotide or expressed from an expression plasmid containing a polynucleotide encoding the protein or peptide. Furthermore the invention includes nucleic acid sequences that encode a targeting moiety selected from γ3, derivatives of γ3 (e.g., 2γ3 or 3γ3), A1, B7, B8, B9, B10, and D6. The invention also includes nucleic acid sequences that encode a peptide of any of SEQ ID NO: 1, 2, 3, 14, 15, 16, 17, 18 or 19. In another embodiment, the targeting moiety is a protein or peptide expressed from a nucleic acid sequence.

Targeting moieties of the invention may be monomeric, dimeric, tetrameric, or any other oligomeric form.

In another embodiment of the invention, the composition comprises more than one targeting moiety, where the composition comprises a targeting moiety that is one or more of γ3, 2γ3, and 3γ3, a variant, derivative or peptidomimetic of γ3, 2γ3, or 3γ3, A1, B7, B8, B9, B10, D6, a variant, derivative or peptidomimetic of A1, B7, B8, B9, B10, or D6, in combination with an antibody, an aptamer, a nucleic acid, a peptide, a carbohydrate, a lipid, a vitamin, a toxin, a component of a microorganism, a hormone, a receptor ligand and any derivative thereof.

In a further embodiment the invention provides a viral, non-viral, bacterial or cell system containing, encoding, expressing, and/or producing a targeting moiety. Such systems may also, optionally, further contain, encode, express, and/or produce an agent. Nucleic acid sequences encoding one or more targeting moieties and/or one or more agents may be present on the same nucleotide sequence or may be present on different nucleotide sequences. Expression of the agent may be co-expression with the targeting moiety or may be separately expressed.

In a still further embodiment, the targeting moiety recognizes a specific target. Such a specific target may include, but is not limited to an antigen or a receptor. In one particular embodiment the specific target is ICAM-1. In one embodiment of the invention, the targeting moiety recognizes both a molecular target isoform present in an animal model (e.g., mice) and also recognizes the human isoform. Preferably the targeting moiety demonstrates an affinity for both human and mouse ICAM-1.

Binding of the targeting moiety to its target molecule on the cell surface is contemplated by the invention for tunable drug carrier delivery and/or transport on the cell surface, intracellularly or transcellularly, as well as interaction with the cell surface target providing secondary protective and/or beneficial effects, e.g., blockage of ICAM-1 binding to leukocytes, fibrinogen/fibrin, and/or pathogens.

In one embodiment the invention provides a delivery composition that comprises a targeting moiety that is capable of binding to ICAM-1. In a further embodiment the targeting moiety binds to human and/or mouse ICAM-1.

The binding of the targeting moiety and ICAM-1 or the transfection, expression, or production of the ICAM-1-targeting moiety may occur in any of cell culture, in vivo, ex vivo or in vitro. The binding may occur such that the targeting moiety binds to and remains on or at the cell surface, such that the targeting moiety binds to and is internalized by cells, or such that the targeting moiety is transported across the cells. Where the targeting moiety is internalized by the cells or transported across the cells, such internalization or transport may progress by any suitable mechanism, including, but not restricted to, endocytosis mechanisms, such as, but not restricted to, CAM-mediated endocytosis.

As a part of fibrinogen/fibrin, γ3 is constitutively present in the circulatory system. Binding of γ3 to ICAM-1 has been shown to decrease inflammation, it has been postulated that γ3 may attenuate atheroclerosis, cancer, and ICAM-1-dependent infections, and there is evidence that γ3 promotes cell survival and anti-apoptotic effects in activated endothelial cells. ICAM-1 is involved in and/or contributes to a variety of maladies or disorders. Such involvement or contribution may include interactions such as binding to ICAM-1, ICAM-1 function, ICAM-1 signaling, CAM-mediated endocytosis (see below) or, generally, ICAM-1-mediated pathways or pathways including ICAM-1 function (where ICAM-1 contributes either solely or in addition to other molecules). Such maladies or disorders include, but are not limited to, inflammation, immune diseases, thrombosis, oxidative stress, and/or certain pathogens, such as acute lung injury, acute respiratory distress syndrome, pulmonary thromboembolism, acute myocardial infarction, ischemic stroke, peripheral vascular pathology, deep vein thrombosis, atherosclerosis, hypertension, diabetes, cancer, AIDS, flu, common cold, poliomyelitis, and malaria.

Accordingly, delivery compositions of the invention, comprising γ3, variants or derivatives thereof (e.g., 2γ3 or 3γ3), A1, B7, B8, B9, B10, and/or D6 are effective in treating such conditions, disorders or maladies. Specifically, in one embodiment, a delivery composition is effective to inhibit inflammation. In another embodiment, a delivery composition of the invention is effective to inhibit lodging of an embolus or inhibit other occlusion of a blood vessel by lodging in the vasculature. Delivery compositions of the invention may also be effective in treating conditions such as bacterial infection, cancer and artherogenesis. The Examples as described herein and set forth in detail below demonstrate the successful conversion of γ3 and phage-display derived peptides into targeting molecules to drive binding, intracellular and transcellular transport of therapeutics and their carriers to cells, and block adhesion of objects to ICAM-1. The Examples further demonstrate the successful inhibition of inflammatory transmigration of leukocytes across endothelial cells and successful in vivo demonstration of inhibition of lodging of fibrin microemboli in the vasculature using compositions of the invention.

As described herein, the invention provides a composition comprising a targeting moiety. In one embodiment the composition is for delivery of an agent to a cell, where the delivery composition includes both a targeting moiety and one or more agents, where the targeting moiety recognizes and binds to a target on a cell and is effective to deliver the agent to the cell. In a further embodiment, the invention provides a delivery composition that includes one or more targeting moieties (recognizing the same or different targets, in the same or different cells) and one or more agents, where one or more of the targeting moieties recognizes and binds to a target on a cell, tissue or organ and is effective to deliver the agent to the cell, tissue or organ.

Target locations may include, but are not limited to, targeting of the kidneys, the spleen, the heart, the lungs, the liver or the brain, and targeting of cells or tissues present in or derived from such organs. The Examples provided herein demonstrate successful in vivo brain transport of therapeutic agent-containing delivery compositions of the invention.

In one embodiment the invention provides a composition comprising an agent such as, but not limited to, research, analytical or molecular probes, diagnostic and therapeutic agents, biologically active agents, research agents, analytical agents, imaging agents, monitoring agents, enzymes proteins, hormones, lipids, sugars, nucleic acids, lipoproteins, and chemicals. In another embodiment, where the agent is an enzyme, it comprises a lysosomal enzyme or encodes for a lysosomal enzyme. Such a lysosomal enzyme may be selected from the enzymes involved in Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, infantile neuronal ceroid lipofuscinosis, and prosaposin. In one embodiment of the invention the agent is acid sphingomyelinase.

The composition may further comprise a delivery carrier for the targeting moiety and/or the agent. In one embodiment, such a delivery carrier is selected from a natural virus or derived viral-like particle, dendrimer, carbon nanoassembly, liposome, a polymer carrier, a microbubble, a paramagnetic particle, a ferromagnetic particle, a self-assembled polymer, a polymersome, a filomicelle, a micelle, a micro particle or nanoparticle, an albumin particle, and/or a lipoprotein.

The elements of the composition may be varied, such as by size and shape, to modulate transport of the composition from the plasma membrane into or across the cells.

In one embodiment the targeting moiety is selected by its size, wherein the size is optimized for delivery to particular destination(s) within a cell. Targeting may be directed to loci such as the lysosome, endosomes, or pathways mediating transport from inside of a target cell to the surface of the cell. Therefore, in one embodiment, the targeting moiety is either below 1 μm size or larger than 1 μm size.

In one embodiment the composition further comprises sodium proton exchanger 1 (NHE1) inhibitors (such as amiloride) or protein kinase C activators (such as phorbol esters) to modulate transport.

Within the composition, the interaction of the elements may occur in a manner providing the most efficient reaction with the target. Accordingly, the interactions may include, but are not limited to, any of the following: the targeting moiety may be coupled to the delivery carrier, the agent may be coupled to the targeting moiety, the agent may be coupled to the delivery carrier, and/or the agent may be coupled to both the targeting moiety and the delivery carrier. The coupling of the elements of the composition may be any effective means of linking, binding, or conjugating the elements. Such interactions may include, but are not limited to, covalent binding, non-covalent binding, binding as a single entity, or binding in combination with one or more other elements of the composition.

The data described herein and reported in the Examples below demonstrate that materials of very different nature and chemistry, size and geometry can safely and efficiently access both human and mouse ICAM-1 when targeted by any of γ3, 2γ3, 3γ3, A1, B7, B8, B9, B10, and D6 and deliver viruses, carriers and agents to the cell surface, as well as into and across cells, via a pathway including ICAM-1 function, operative in a variety of cell types in control and disease conditions.

In one embodiment the invention provides compositions and methods useful in both laboratory experimentation and clinical endeavors. The compositions and methods of the invention are applicable in in vivo, ex vivo and in vitro applications, including cell cultures, animal models, human application or administration, and the like.

Comparison was made of γ3, 2γ3, 3γ3, A1, B7, B8, B9, B10, and D6 expressed onto viruses or coupled to prototype polystyrene carriers, biodegradable FDA-approved material-PLGA carriers, and carriers bearing therapeutic enzymes (recombinant acid sphingomyelinase, ASM) vs IgG-, anti-ICAM- and γ3-derived or A1-derived scramble peptide counterparts and ligands of classical endocytic pathways, and non-targeted counterparts, in terms of binding, transport, and effects, both in cell cultures and animal models.

In Example 1, in vivo accessibility of ICAM-1 was compared to that of determinants of clathrin and caveolar pathways, which also mediate transport into and across cells. As an example, antibodies to transferrin receptor and GM1, associated to clathrin pits and caveoli, only gained access to lung endothelium when injected iv in mice as free counterparts, not on 180 nm carrier particles (FIG. 1A), likely due to size limits of clathrin pits and caveoli and/or distribution of their receptors. ICAM-1 was accessible to both free targeting moieties (antibodies) and preferential carriers, which were specific against control IgG carriers (FIG. 1A). ICAM-1 targeting increased in a disease mouse model (ASM knockout (KO) mice), likely due to ICAM-1 overexpression described in many pathologies, while accumulation of free ASM, an enzyme that binds to mannose-6-phosphate receptor associated to classical clathrin pathways, was 10-fold lower and was further decreased in the disease model (FIG. 1B). This could be due to reduced endocytic uptake via classical pathways in disease conditions, as Niemann-Pick A/B-patient cells and ASMKO-mice cells had reduced uptake of ligands, toxins, and particles by clathrin pits, caveoli, macropinocytosis, and phagocytosis (FIG. 1C). Endocytic defects were also observed in other diseases, including Fabry, Gaucher and Niemann-Pick C (FIG. 1D). Yet, CAM-endocytosis of ICAM-1-targeted carriers was as efficient as in control cells (FIG. 1C). Also, ICAM-1-targeted particles of various sizes (up to 5 μm) and shapes (spheres, elliptical disks, and polymorphous conjugates) could access ICAM-1 targets in vivo and be efficiently endocytosed in cell culture (FIG. 1E).

In Example 2, ICAM-1-targeting moieties were shown to stably target the cell surface (anti-ICAM in FIG. 2A) and intracellular compartments (anti-ICAM polystyrene nanocarriers in FIG. 2B) in cell culture, as well as in vivo after iv injection in mice (anti-ICAM polystyrene carriers in endosomes and lysosomes in FIG. 2C left), where they were also safely transported across endothelial cells layers transcellularly without disruption of the cell junctions (FIG. 2C right). The final destination of these carriers, to compartments within the cell or re-surfacing to the exterior of the cell (adequate for intracellular vs transcellular delivery) can be controlled by the size of the carriers (FIG. 2D).

Figure 3:
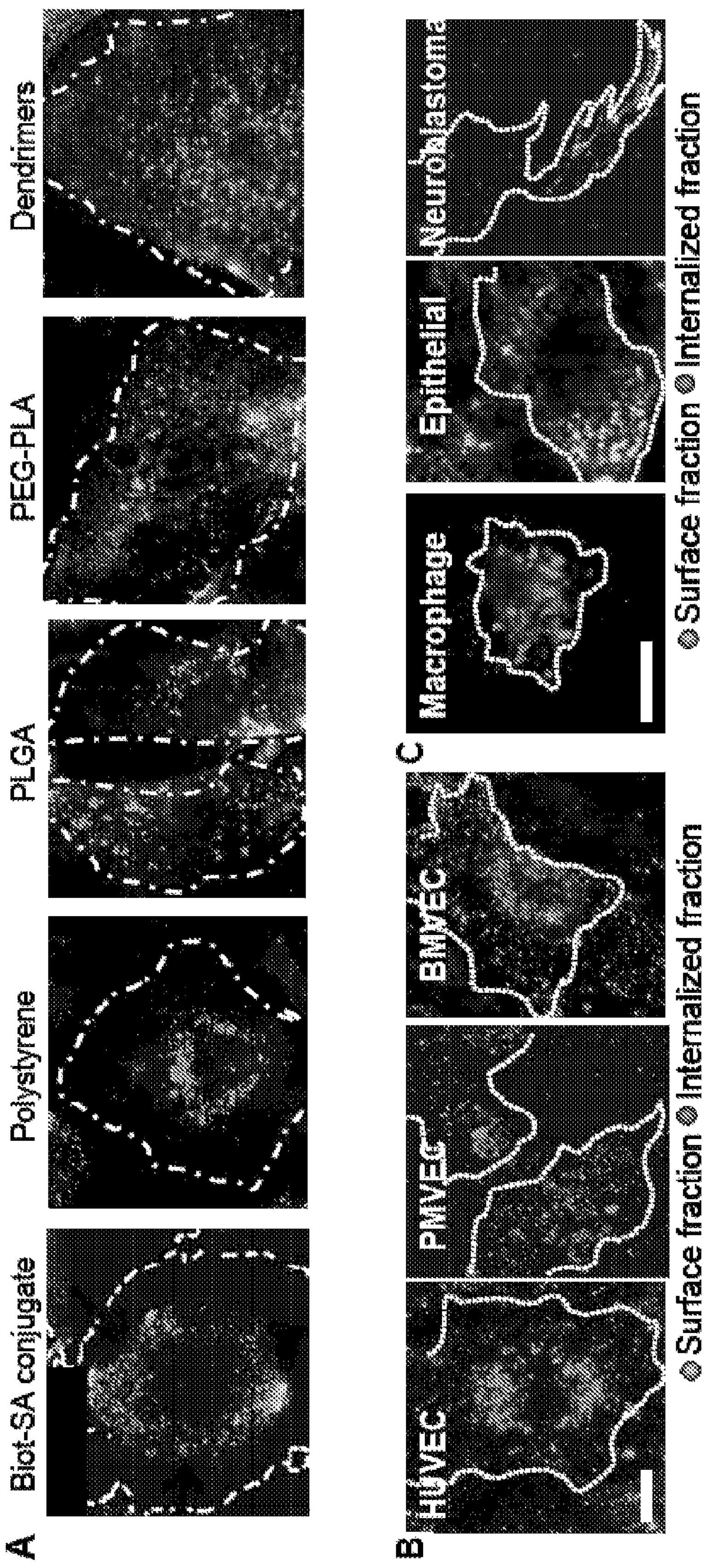
FIG. 3 illustrates the results of Example 3, showing efficient targeting and internalization of various delivery compositions and various cell types.

Example 3 demonstrates broad utility of ICAM-1-mediated targeting and transport for a variety of drug delivery systems and cell types. ICAM-1-targeted systems were tested, including biotin-streptavidin conjugates, polystyrene particles, PLGA carriers, poly-ethylene glycol poly-lactic acid (PEG-PLA) carriers, and natural polymer dendrimers, were efficiently internalized by cells in culture (FIG. 3A); and all tested endothelial cells, such as lung and brain endothelium, from macro- and micro-vascular beads, of mouse and human origin (FIG. 3B), and also by non-endothelial cells, including macrophages, alveolar epithelial cells, and neuroblastoma cells (FIG. 3C). Hence, altogether this series of experiments demonstrate the efficacy and versatility or ICAM-1 targeting in the context of delivery of drug carriers in cell cultures and in vivo, to different sub-cellular environments, in control and diseased conditions.

Figure 4:
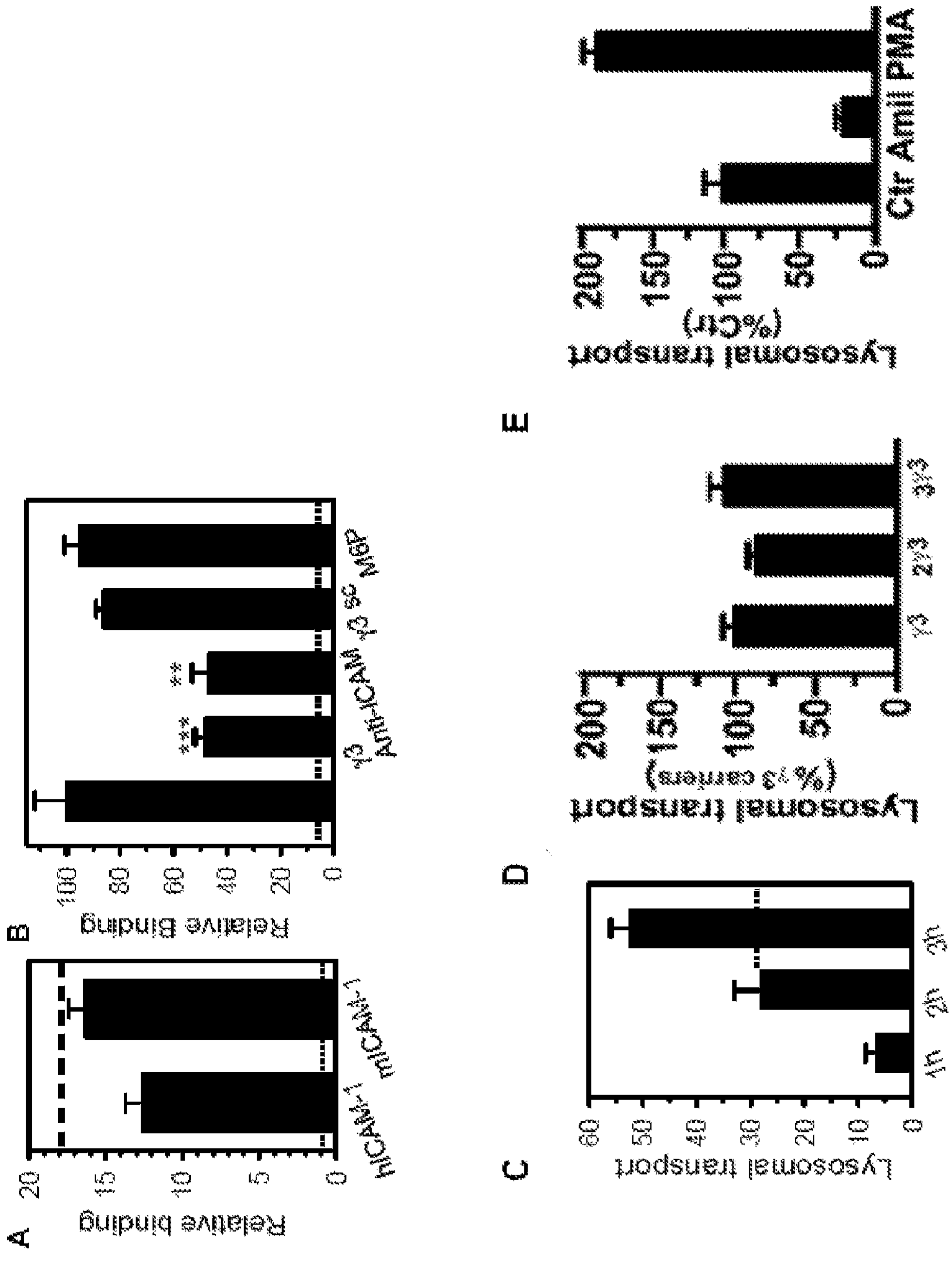
FIG. 4 illustrates the results of Example 4, where FIG. 4A provides a graph of the relative binding of γ3 carriers to both human and mouse ICAM-1, and as compared to anti-ICAM carriers.

Example 4 demonstrates efficient and specific binding and intracellular transport of therapeutic carriers to human and mouse ICAM-1 via the affinity peptide γ3 and its derivative peptides 2γ3 and 3γ3. Furthermore, synthetic peptide γ3 was absorbed on 100 nm FITC polystyrene particles and the resulting carriers efficiently bound to immobilized human ICAM-1/Fc (as expected) but also, surprisingly, to mouse ICAM-1/Fc, vs to control immobilized albumin (FIG. 4A). Binding was similar to than of anti-ICAM carriers (FIG. 4A). Hence, γ3 can be used in mouse and human models and settings. The γ3 carriers also bound to native ICAM-1 expressed by both activated human and mouse endothelial cells, but not control 293 cells which are known to be voided of ICAM-1 expression (FIG. 4B). Importantly, co-absorption of the therapeutic enzyme ASM with γ3 on the carrier surface did not affect targeting to human or mouse endothelial cells (FIG. 4B). Targeting to these cells was similarly suppressed by excess of free γ3 peptide or anti-ICAM in the media, but not by a peptide with a scrambled γ3 sequence (FIG. 4B). Excess free mannose-6-phosphate (MP6) in the media did not compete for carrier binding to cells, either, indicating that M6P residues in ASM did not contribute to targeting (FIG. 4B).

The γ3/ASM polystyrene carriers were internalized by human and mouse endothelial cells at 37° C., and after uptake, γ3/ASM carriers trafficked to lysosomes in the perinuclear region of the cell, shown by co-localization with dextran-labeled lysosomes in HUVEC (FIG. 4C). Binding and internalization leading to lysosomal transport was similar for carriers targeted to ICAM-1 by either γ3 or their derivatives 2γ3 and 3γ3 (FIG. 4D). Endocytic transport was inhibited by amiloride and activated by phorbol esters activating protein kinase C or PKC, confirming a CAM-mediated mechanism (FIG. 4E). Hence, γ3 carriers elicit the same unique pathway than anti-ICAM carriers, crucial to effectively deliver therapeutics intracellularly and across cells.

Figure 5:
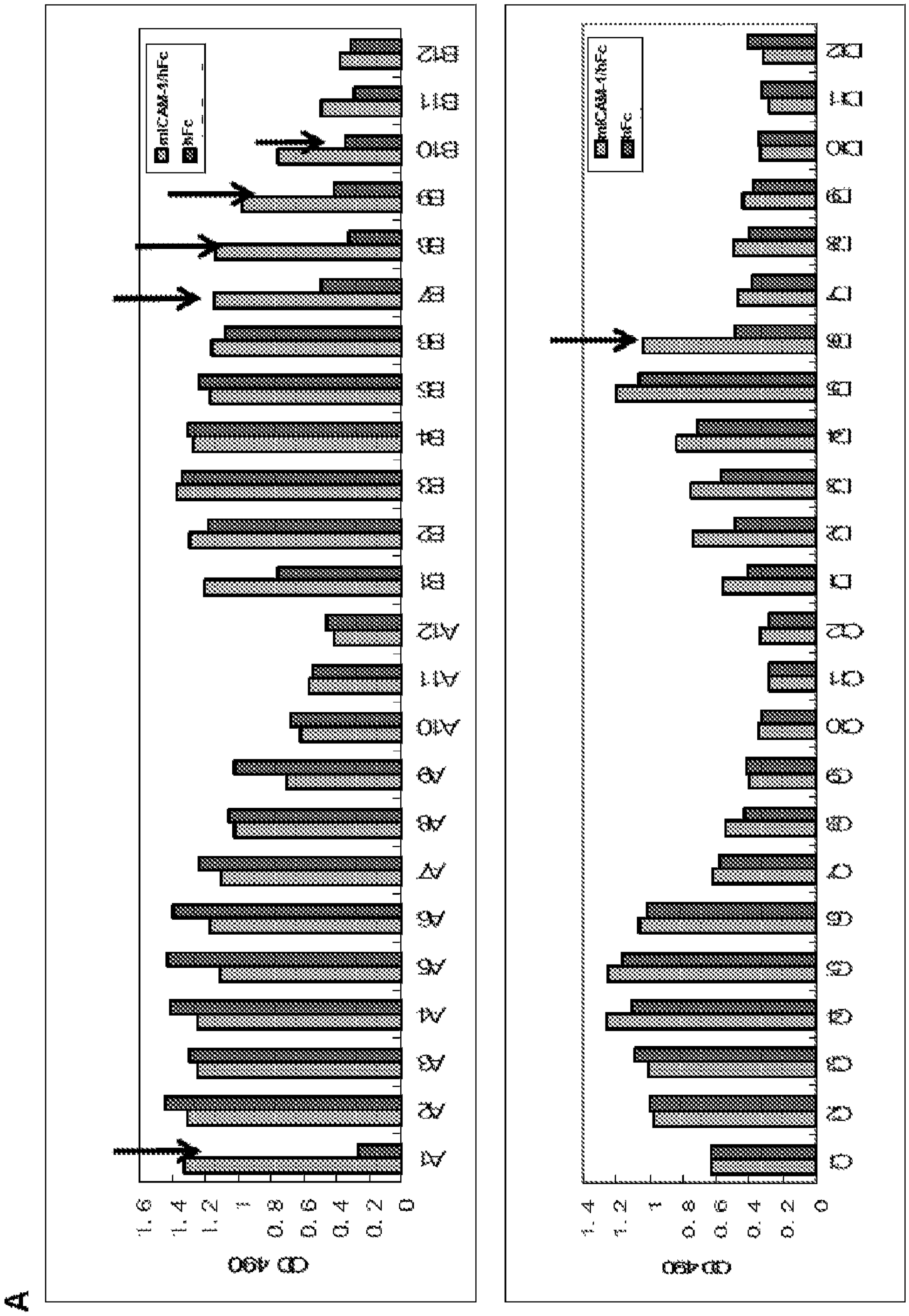
FIG. 5 illustrates the results of Example 5, demonstrating efficient and specific binding of various ICAM-1-targeting moieties or viruses expressing these moieties to human and mouse ICAM-1 via peptides A1, B7, B8, B9, B10 and D6 as targeting moieties.
Figure 5:
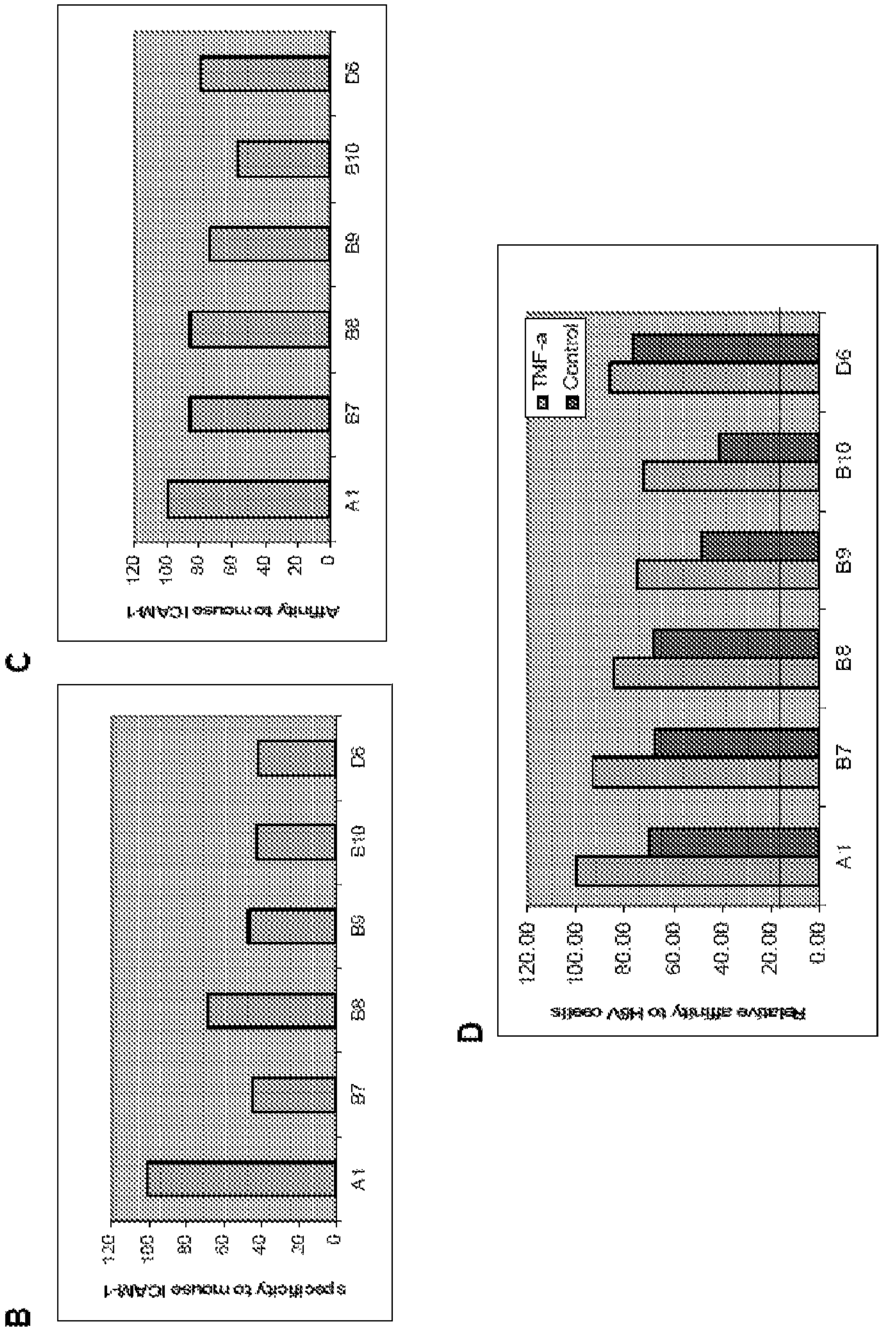
Figure 5:
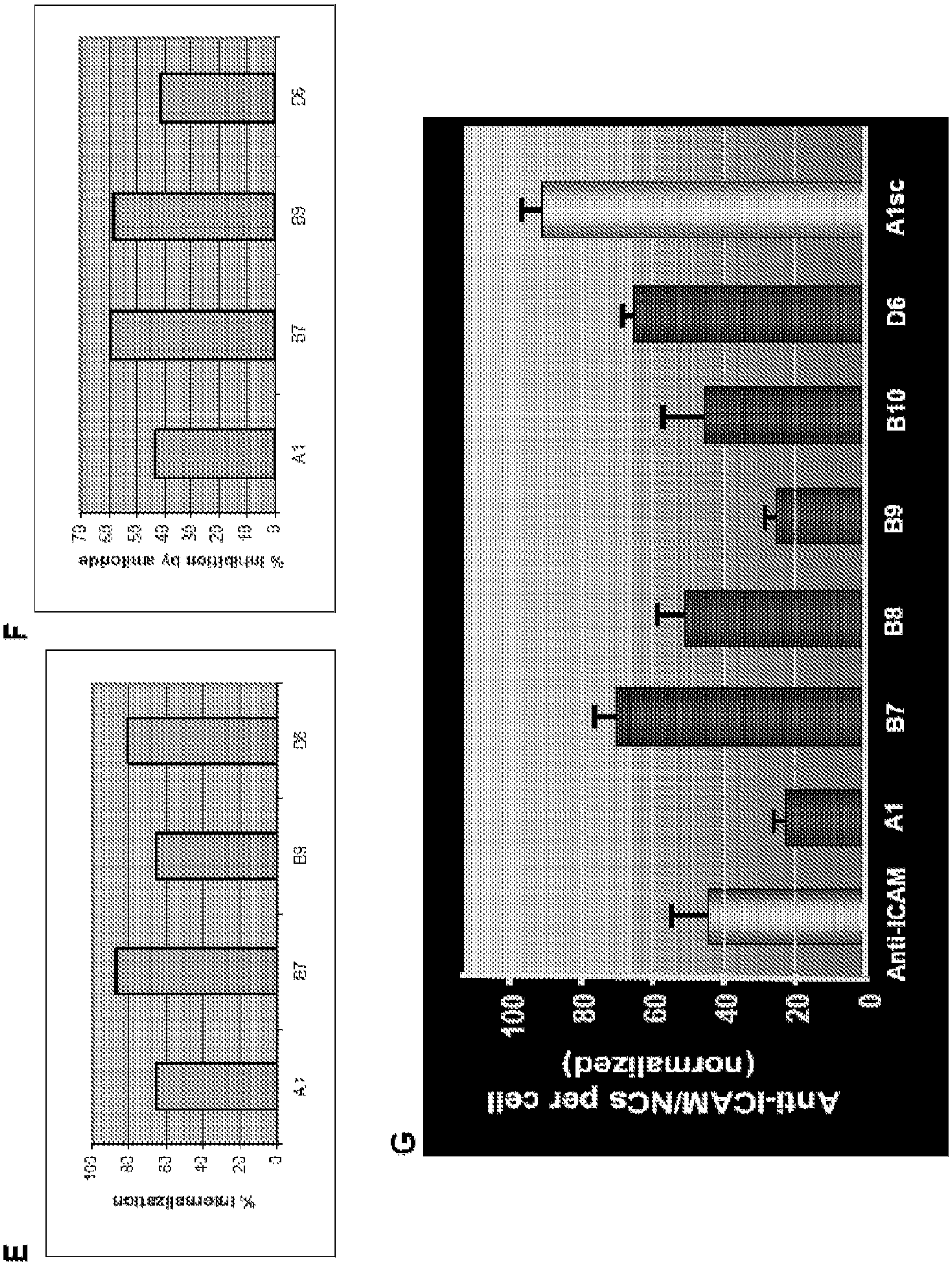

Example 5 details development of the 7-mer phage-display derived peptides against ICAM-1. These were identified and isolated from a random library by using a chimeric ICAM-1 protein consisting of the two most membrane-distal Ig domains of mouse ICAM-1 fused to human Fc (hFc). One round of negative selection against hFc, followed by three rounds of positive selection against mouse ICAM-1/hFc, rendered six phage clones (A1, B7, B8, B9, B10, and D6), which recognized immobilized mouse ICAM-1 (FIG. 5A). Specificity vs hFc was higher for A1 (~5.1 fold), followed by B8>B7>B9>B10>D6 (68.6%-41.2% of A1) (FIG. 5B). A1 clone presented the highest affinity to immobilized mouse ICAM-1 (~4.7 fold over non-selected phages), followed by B7>B8>D6>B9>B10 clones (85.7%-56.7% of A1) (FIG. 5C). All six clones recognized native ICAM-1 expressed by mouse endothelial cells (H5V) as compared to control 293-ICAM-1 negative-cell type. In this setting, also A1 phage clone presented the highest affinity followed by D6>B10>B7>B8>B9 clones (92.9%-72.3% of A1) (FIG. 5D). Binding to cells increased up to 1.8 fold by TNFα, a cytokine which up-regulates ICAM-1 expression (FIG. 5D).

In addition, fluorescence microscopy showed that phage viruses expressing 5 copies of the peptides A1, B7, B9, or D6 (but not B8 or B10) on their capsid were internalized by endothelial cells at 37° C. (65-87% internalization, 1 h) but not at 4° C., indicative of endocytosis (FIG. 5E). This process was inhibited by amiloride (41-59% inhibition) (FIG. 5F), which has been shown in the past to interfere with CAM-mediated endocytosis. Therefore, these peptides are also adequate for either stable delivery to the cell surface, or intracellular delivery.

Surprisingly, clone A1 phages also strongly recognized immobilized human ICAM-1/hFc and native human ICAM-1 expressed by human endothelial cells (HUVEC), (~70% affinity of mouse ICAM-1). A1 peptide synthesized in vitro (but not control A1 scramble peptide), as well as B9 (and at some extent B8 and B9) competed binding of anti-ICAM nanocarriers to human endothelial cells (~80% inhibition) (FIG. 5G). This is a crucial finding, since it provides the opportunity to utilize these peptides in mouse and human cells and settings, and potentially in future clinical trials. Also, this demonstrates that ICAM-1-targeting peptides can block binding of other objects to ICAM-1, e.g., for applications such as beneficial blockage of binding of leukocytes, fibrinogen/fibrin, and/or pathogens to ICAM-1.

Example 6 demonstrates in vivo pharmacokinetics and biodistribution of therapeutic carriers targeted to ICAM-1 via the affinity peptide γ3 and its derivative peptides 2γ3 and 3γ3. In animal model tests, the γ3 2γ3 or 3γ3 carriers, coupled to therapeutic ASM, bound specifically and efficiently to, and were endocytosed by, endothelium in vivo in mice. They rapidly disappeared from the bloodstream (FIG. 6A), which was not a consequence of rapid clearance by the reticuloendothelial system (as in the case of clearance of control IgG/

Figure 6:
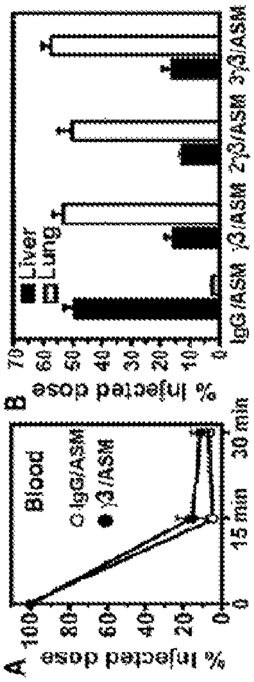
FIG. 6 illustrates the in vivo pharmokinetics and biodistribution of γ3, 2γ3 and 3γ3 targeting moieties on carriers targeting therapeutic agents targeting ICAM-1, as provided in Example 6.
Figure 6:
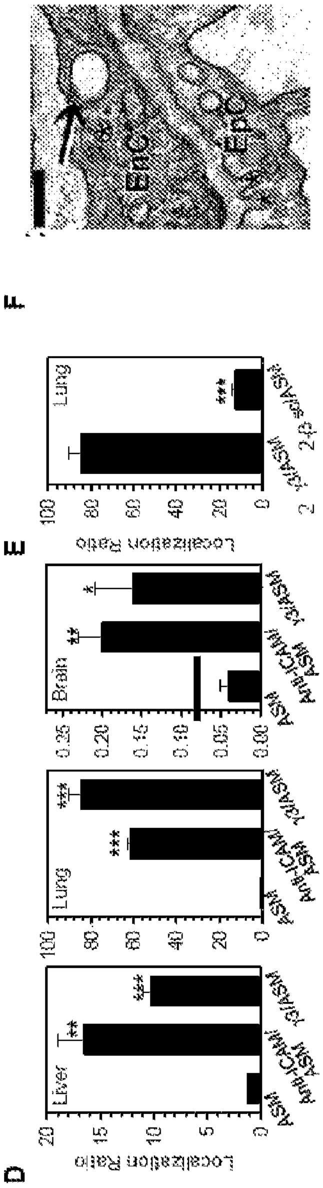

ASM carriers by the liver) but rather a consequence of rapid targeting to organs, e.g., the lungs, after i.v. injection in mice (FIG. 6B). Indeed, γ3 2γ3 or 3γ3 carriers enhanced the delivery of ASM vs than of free ASM in all organs, including brain, kidneys, spleen, liver, heart, and lungs, and 2γ3 or 3γ3 carriers showed lower lung deposition and greater brain deposition than γ3 carriers (specificity index, FIG. 6C) This is the first time that test brain targeting of ICAM-1 strategy has been examined and surprisingly its efficacy was found to be higher than the one reported for strategies of targeting to determinants commonly used for brain delivery, such as the case of insulin receptor or transferrin receptor: targeting to insulin receptor of α-L-iduronidase=0.02% injected dose per gram (% ID/g) versus ICAM-1 targeting of ASM prototype carriers=0.2% ID/g in brain.

Accumulation of ASM delivered by γ3, 2γ3 or 3γ3 carriers to this organs was comparable to that of ASM delivered by anti-ICAM carriers (FIG. 6D). This is readily clear from the localization ratio of these formulations, which represents the ratio between the % injected dose per gram of organ and that in circulation. Since the estimated dose measured in a given organ also include that of the blood irrigating that organ, the localization ratio permits to normalize data to the different levels of circulating materials. For instance, ASM lacks affinity and results in high circulating levels compared to ICAM-1 targeted formulations that rapidly bind to endothelium and disappear from blood. ASM targeting in vivo to ICAM-1 by the γ3-strategy was specific, as shown by lack of targeting of 2γ3-scramble/ASM carriers, or that of 2γ3/ASM carriers in ICAM-1 KO mice (FIG. 6E). Importantly, targeting to ICAM-1 with biodegradable PLGA carriers by the γ3-strategy resulted in CAM-mediated endocytic transport in vesicular compartments in endothelium in vivo (e.g., 2γ3/ASM PLGA carriers in FIG. 6F).

Example 7 demonstrates the therapeutic effects of cargoes intracellularly delivered to patient cells by γ3-strategy carriers (Table 1).

As an example of the therapeutic utility of this strategy, the effects of ASM targeting were compared to ICAM-1 using anti-ICAM vs the γ3-strategy provided herein. Recombinant ASM is used for enzyme replacement therapy of patients of types A and B Niemann-Pick disease, where genetic mutations lead to ASM deficiency and intracellular lysosomal accumulation of sphingomyelin and cholesterol, resulting in cell dysfunction, multi-organ complications, and often a fatal outcome. (He X., et al., *Anal. Biochem.* 2003; 314:116-20; Schuchman E. H., and Muro, S., *The development of enzyme replacement therapy for lysosomal diseases: Gaucher disease and beyond.* In: Futerman A H, ed. Gaucher disease: Lessons learned about therapy of lysosomal disorders: CRC Press.; 2006:125-40.) It has been previously shown by the present inventors that anti-ICAM carriers deliver active ASM to lysosomes in cells from Niemann-Pick patients, attenuating sphingomyelin and cholesterol storage to control values, vs free ASM which only partially attenuates the levels of these lipids. Similar levels of degradation of these lipids were achieved by targeting ASM to ICAM-1 via the present γ3 strategy, using either prototype polystyrene carriers or biodegradable PLGA carriers (Table 1).

Example 8 provides a strategy for the design of a chimeric therapeutic enzyme containing ICAM-1-targeting γ3, 2γ3 or 3γ3 derivative peptides, or A1, B7, B8, B9, B10, or D1 peptides.

Figure 7:
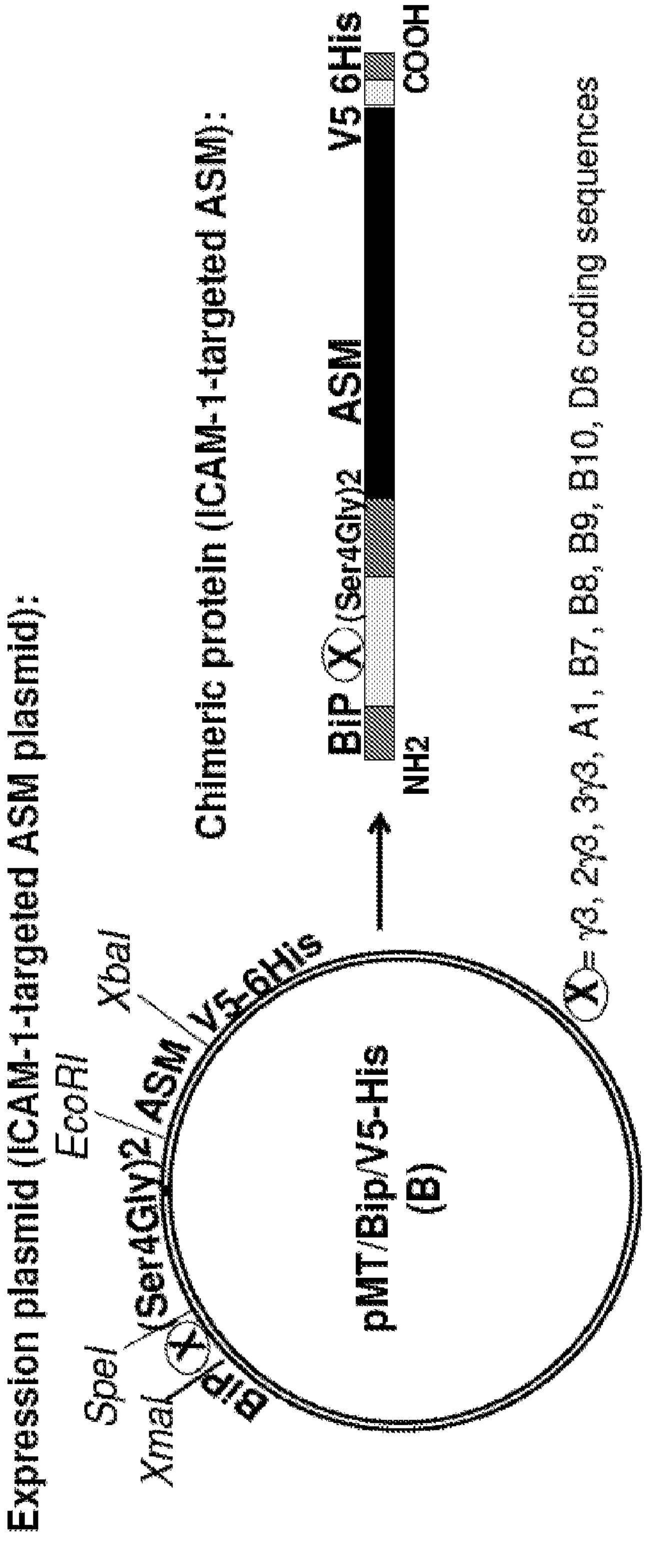
FIG. 7 illustrates the ICAM-1-targeting ASM plasmid (B), as utilized in Example 8, where the plasmid contains a coding sequence for any of γ3, derivatives of γ3 (e.g., 2γ3 or 3γ3), A1, B7, B8, B9, B10, and D6.

Further, direct coupling of γ3, 2γ3, 3γ3, A1, B7, B8, B9, B10, and/or D6 peptides (or their nucleotide encoding sequences) to therapeutic or diagnostic agents, via biotin-streptavidin, chemical conjugation, covalent coupling, through antibodies, or direct synthesis (e.g., chimeric proteins or their coding sequence for gene expression via plasmid, viral or non-viral vectors), is contemplated for utility for ICAM-1 targeting and transport to cells or the body in vivo. As an example, FIG. 7 shows the design of a therapeutic chimeric enzyme produced from a plasmid containing γ3, 2γ3 or 3γ3 sequences cloned at the amino-terminus of the ASM sequence, separated by a (Ser4-Gly)2 peptide spacer to allow independent folding and the targeting and enzymatic moieties of the chimera. This cassette can be cloned in a pMT/BiP/V5-His (B) plasmid for amplification under ampicilin selection in *E. coli* and expression in S2 insect eukaryotic cells, which will allow for expression under metallothionein promoter upon induction by copper sulfate, traffic of the chimeric enzyme through the secretory pathway due to presence of BiP, and extracellular secretion after BiP cleavage by S2 cells. The chimeric enzyme, which contains V5 sequence and 6His tag fused to the carboxyl terminus, can be purified using a Ni-chelating resin. The resulting protein (~80 kDa) can be separated by SDS-PAGE and blotted with anti-V5 to trace the V5-tag. Possible modifications of this design include elimination of the BiP, V5 and/or His-tag sequences, elimination of change of the linker, cloning of the targeting peptide in the carboxyl-terminus of ASM, exchange of the ASM coding sequence for another therapeutic gene, siRNA, or cloning of the targeting peptide with no cargo, tandem repeats of the targeting peptide to allow for multivalency of ICAM-1 targeting, inclusion of interacting peptides or sequences to promote dimerization, tetramerization, or formation of oligomers of the peptides or the chimera, and to provide multivalent targeting to ICAM-1, cloning into other vectors for expression under different selection markers, in different cell types, in bacteria, by viruses, for enzyme or gene therapy, among other modifications.

Figure 9:
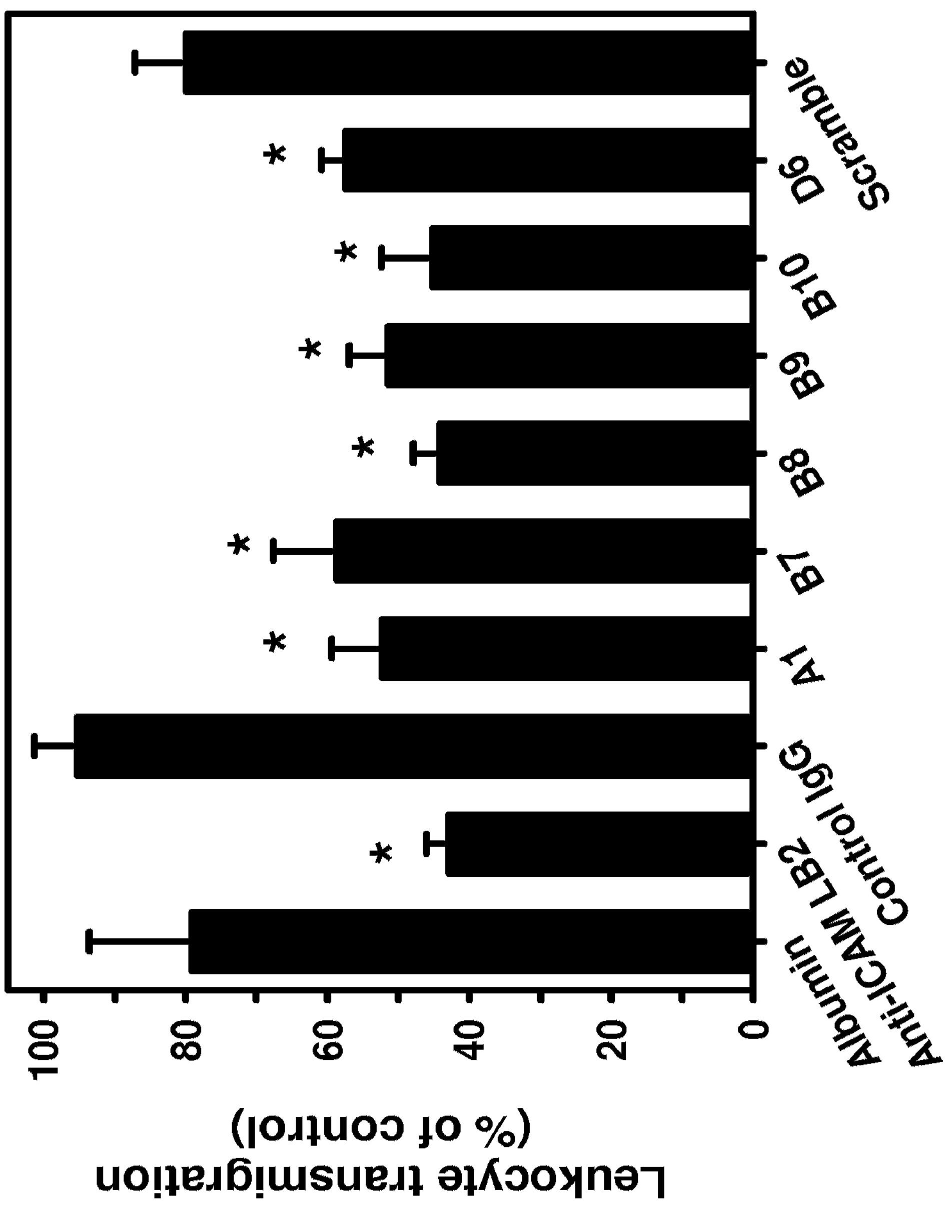
FIG. 9 is a graphical illustration of inhibition of leukocyte transmigration across endothelial cells by various ICAM-1-targeting peptides, as described in Example 10 hereof.

Example 9 provides in vivo brain transport of a composition of the invention in a mouse model, where the composition contains 2γ3/ASM and PLGA. FIG. 9 is transmission electron microscopy pictures showing successful migration of the compositions across the blood-brain barrier.

Example 10 provides inhibition of inflammatory leukocyte transmigration across endothelial cells by ICAM-1-targeting peptides A1, B7, B8, B9m B10 and D6. All were shown (FIG. 9) to inhibit leukocyte transmigration, when compared to the controls (albumin (negative control), scrambled peptide (negative control) and LB2 (positive control)).

Example 11 provides in vivo inhibition of lodging of fibrin microemboli in the vasculature of mice by administration of ICAM-1-targeting peptide γ3, resulting in continued circulation of the fibrin microemboli, rather than lodging in the vasculature or other organ.

Therefore, it is possible to safely and effectively target therapeutics and their carriers (including viruses) to both human and mouse ICAM-1, in a variety of cell types in culture and in vivo in animals and animal models, using the γ3 peptide, derivative peptides 2γ3 or 3γ3, and/or phage-derived peptides A1, B7, B8, B9, B10, or D6. This provides either stable binding to the cell surface and/or further transport to intracellular compartments and/or across cells for penetration in the tissues, with delivery of active compounds providing therapeutic benefits, as in the case of enzyme therapies and/or gene therapies for lysosomal disorders (see U.S. Provisional Patent Application 60/584,648). Exemplary carriers for safe transport of materials from intracellular compartments such as endosomes into the cell cytosol and nucleus are described in U.S. Provisional Patent Application 60/931,552. The present ICAM-1-targeting strategy in combination with these carriers have general applicability for delivery to these cell compartments. Since ICAM-1 is expressed in the diverse cell types in the body, including epithelial cells lining most of body cavities and entry routes (e.g., epithelial cells in the airways and alveoli, epithelial cells in the gastrointestinal tract, mesothelial cells in the pleura, and epithelial cells lining joints and ventricles in the CNS), muscle cell, glial and neuronal cells, etc., this strategy can be used for delivery of drugs to all of these compartments in the body. Furthermore, delivery is likely to be enhanced under pathological conditions due to overexpression of ICAM-1 and ICAM-1 blocking may be additionally beneficial (anti-inflammatory effects, anti-thrombotic by preventing deposition of fibrinogen and/or fibrin). Similar methods could be applied for intracellular delivery of drugs, biosensors, research, analytical, imaging, diagnostic and therapeutic agents, either in the context of research or clinical applications.

The advantages and features of the invention are further illustrated with reference to the following examples, which are not to be construed as in any way limiting the scope of the invention, but rather as illustrative of various embodiments of the invention in specific applications thereof.

Example 1

Efficacy and Versatility of Targeting to and Transport Mediated by ICAM-1 vs Determinants of Classical Endocytic Pathways (A) Lung uptake (30 min) of $^{125}$I-labeled anti-transferrin receptor (targeted to the clathrin route), anti-GM1 (anti-ganglioside GM1, targeted to caveoli), or anti-ICAM, injected intravenously in mice as free antibodies or absorbed on the surface of 100 nm polystyrene particles (prototype carrier final size=180 nm). Particles had $^{125}$I-labeled IgG as a tracer. Dashed line=control unspecific IgG carriers. (B) Lung uptake (30 min) of radiolabeled acid sphingomyelinase, a recombinant enzyme which binds to mannose 6 phosphate (M6P) receptor, vs anti-ICAM polystyrene carriers in control C57Bl/6 mice vs diseased ASMKO mice. Data is normalized per gram due to larger lung size in ASMKO mice. Dashed line=anti-ICAM carriers injected in control ICAM-1 KO mice, which do not express ICAM-1. (C) Endocytosis (1 h-37° C.) of fluorescent transferrin (targeted to the clathrin route), cholera toxin B (targeted to the caveolar route), EGF-induced dextran (macropinocytosis), and 180 nm anti-ICAM polystyrene carriers (CAM-endocytosis) by fibroblasts from patients of type A-B Niemann-Pick, or 1 μm IgG-coated particles (phagocytosis) by diseased ASMKO alveolar macrophages, analyzed by fluorescence microscopy. (D) Internalization (1 h-37° C.) of fluid-phase Texas-red dextran by skin fibroblast from Fabry, Gaucher, type C Niemann-Pick (NPC) and NPD patients, characterized by deficiency of α-galactosidase-A, glucocerebrosidase, NPC1 transporter, and ASM, respectively. (E) FITC-labeled anti-ICAM carriers of diverse geometry (anti-ICAM polystyrene spheres from 0.1 to 5 μm or 0.1×1×3 μm elliptical disks, and polymorphous anti-ICAM conjugates formed by biotin-streptavidin crosslinking were incubated with TNFα activated human umbilical vein endothelial cells (HUVEC) for 1 h at 37° C. The cells were then washed and fixed, cell surface-located carriers were differentially stained with a texas red-conjugated secondary antibody, and the samples were analyzed by fluorescence microscopy to quantify the percent of carriers internalized by the cells. Data are mean±standard error of the mean for n≥4 mice or ≥20 cells. *p<0.05, p<0.005, *p<0.001 by student's t test.

Example 2

Transport to Different Sub-Cellular Environments Via ICAM-1 Targeting (A) TNFα activated HUVEC were incubated for 1 h at 37° C. with anti-ICAM antibody, then non-bound antibodies were washed and cells were stained with a secondary antibody conjugates to texas red, only accessible to cell surface-located anti-ICAM, to detect the antibody fraction that remained in the plasma membrane. Then, cells were permeabilized and stained with a secondary antibody conjugated with green FITC, which would be accessible to both surface and internalized anti-ICAM. After analysis by fluorescence microscopy, cell surface antibodies were visualized both under the green and red channels, indicated by yellowish fluorescence, whereas no green internalized antibodies were observed. (B) HUVEC were incubated for 1 h at 37° C. with anti-ICAM antibodies absorbed on the surface of 100 nm FITC-labeled polystyrene nanocarriers. Cells were then washed, fixed, and stained with texas red secondary antibody which can only detect accessible surface anti-ICAM carriers. After analysis by fluorescence microscopy, internalized carriers were visualized under the green channel in the perinuclear region of the cell, whereas no yellowish carriers on the cell surface were observed. Dashed lines in (A) and (B) mark the cell border, determined by phase-contrast microscopy. (C) Anti-ICAM/ASM polystyrene carriers were injected in anesthetized C57Bl/6 mice. Five hours after injection, the animals were perfused and fixed through the left ventricle under ventilation, and the lungs were isolated and processed for transmission electron microscopy. Arrows=endothelial cell (EC) surface-bound carriers. White arrowhead=carriers in an intracellular endosome. Black arrowheads=carriers in intracellular lysosomes. Grey arrowhead=intact cell junctions. Asterisks=caveoli. Bordered arrowheads=carriers transported across the endothelial layer into epithelial cells in the alveoli. Scale bar=100 nm. (D) Activated HUVEC were incubated for 30 min at 4° C. with FITC-labeled anti-ICAM polystyrene carriers (spherical 180 nm or 1 μm, or discoidal 0.1×1×3 μm) to only allow binding, following by washing and endocytosis of pre-bound particles for 1 h (not shown) or 5 h at 37° C. The cells were then fixed and the presence of particles containing intact anti-ICAM coat on the cell surface was assessed by immunostaining using a Texas-red secondary antibody. Since after 1 h incubation no red+green (yellow) particles were visualized in the cell surface, the appearance of such particles at later times indicate recycling from intracellular compartments, quantified by fluorescence microcopy. *p<0.05, by student's t test.

Example 3

Broad Utility of ICAM-1-Mediated Targeting and Transport for a Variety of Drug Delivery Systems and Cell Types (A) TNFα activated HUVEC were incubated for 1 h at 37° C. with anti-ICAM conjugates prepared by coupling via streptavidin biotinylated anti-ICAM, anti-ICAM polystyrene nanocarriers, anti-ICAM poly-lactic co-glycolic acid (PLGA) nanocarriers, anti-ICAM poly-ethylen glycol (PEG) poly-lactic acid (PLA) nanocarriers, or biopolymeric dendrimers. Non-bound conjugates and carriers were washed, the cells were fixed, stained and analyzed as described in FIG. 2A-B. (B) Internalization of 100 nm FITC-labeled (green) anti-ICAM polystyrene carriers by TNFα-activated macrovascular human umbilical vein endothelial cells (HUVEC), mouse pulmonary microvascular endothelial cells (PMVEC), human brain microvascular endothelial cells (BMVEC), and (C) mouse peritoneal macrophages, human alveolar epithelium-derived EAhy926, and human neuroblastoma SH-SY5Y. In all pictures cell surface-bound materials are shown in red+green double labeled color (yellowish) vs internalized materials which appear as single labeled in the green channel. Dashed lines mark the cell border, determined by phase-contrast microscopy. Magnification bar=10 μm.

Example 4

Efficient and Specific Binding and Intracellular Transport of Therapeutic Carriers to Human and Mouse ICAM-1 Via the Affinity Peptide γ3 and its Derivative Peptides 2γ3 and 3γ3

(A) The peptide γ3 was absorbed on the surface of 100 nm FITC-labeled polystyrene carriers and the resulting products were incubated for 15 min on nitrocellulose-immobilized albumin vs human or mouse ICAM-1 chimeras containing ICAM-1-Ig domains 1 and 2 fused to human Fc sequence. The membranes were washed and analyzed by fluorescence microscopy to quantify the number of carriers bound per area. Data are expressed relative to non-specific binding of γ3 carriers to albumin controls (dotted line). A comparison to binding of anti-ICAM carriers is provided (dashed line). (B) Binding of FITC-labeled polystyrene carriers coated by absorption with the peptide γ3 and recombinant acid sphingomyelinase (ASM, a therapeutic enzyme) to activated HUVEC (bars) vs ICAM-1-negative 293 cells (dotted line) was quantified by fluorescence microscopy after 1 h incubation at 37° C., in the absence or presence of excess γ3, anti-ICAM, γ3 scramble peptide, or mannose 6 phosphate (M6P). Data is shown relative to HUVEC binding of γ3/ASM carriers (134±11 particles/cell). (C) HUVEC lysosomes were labeled for 2 h with Texas-red dextran at 37° C. Cells were then incubated for 30 min at 37° C. with FITC-labeled γ3/ASM carriers, non-bound carriers were washed, and incubation was continued up to 1, 2, or 3 h. Co-localization of FITC carriers with Texas-red dextran-lysosomes was quantified by fluorescence microscopy. (D) Comparison of lysosomal transport of 100 nm FITC-labeled polystyrene carriers coated with either ICAM-1-targeting peptide γ3 vs its derivatives 2γ3 and 3γ3. (E) Activated HUVEC were incubated for 30 min at 37° C. in the presence of FITC-labeled 2γ3 polystyrene carriers after 15 min pre-treatment with 3 mM amiloride to block ICAM-1-mediated endocytosis, or 0.1 μM PMA to activate PKC and promote ICAM-1-mediated endocytosis. Co-localization of FITC 2γ3 carriers with Texas red dextran-labeled lysosomes was assessed by microscopy 3 h post-internalization. Mean±SEM; n=2 assays. $^{}p<0.005$, $^{*}p<0.001$, by student's t test.

Example 5

Efficient and Specific Binding and/or Intracellular Transport of Peptides or Peptide-Expressing Viruses to Human and Mouse ICAM-1 via the Affinity Peptides A1, B7, B8, B9, B10, AND D6

(A) ELISA measurement of the binding of 7-mer peptide expressing phage library to immobilized recombinant ICAM-1 (consisting of the two most membrane-distal Ig domains-1 and 2- of mouse ICAM-1 fused to human Fc or hFc), versus their binding to control hFc. (B) Relative specificity and (C) relative affinity of ICAM-1-targeting peptide phages, determined by ELISA from the experiment in (A). (D) Relative binding of phages expressing 7-mer peptides to native ICAM-1 expressed on the surface of HV5 mouse endothelial cells, either control or activated with TNFalpha to mimic a disease phenotype. Binding was determined by microscopy using a fluorescently-labeled antibody to the phage capsid. The line in the graph indicates the level of binding of A1 phage to 293 cells, which are voided of ICAM-1-expression. (E, F) Endocytosis (1 h, 37° C.) of phages expressing 7-mer peptides by control mouse endothelial cells (E) or mouse endothelial cells incubated in the presence of 3 mM amiloride (F) was estimated by microscopy after staining surface-located phages with a Texas red-labeled antibody to the viral capsid, following by cell permeabilization and staining of all (surface and internalized) phages using a FITC-labeled antibody to the viral capsid. (G) Binding of FITC-labeled anti-ICAM polystyrene nanocarriers to human endothelial cells was evaluated by fluorescence microscopy after incubation with cells in the absence (100% level) or presence of anti-ICAM antibody, ICAM-1-targeting synthetic peptides, or peptides with their scramble sequence (e.g., A1sc).

Example 6

In vivo Pharmacokinetics and Biodistribution of Therapeutic Carriers Targeted to ICAM-1 via the Affinity Peptide γ3 and its Derivative Peptides 2γ3 and 3γ3

IgG/$^{125}$I-ASM polystyrene carriers vs γ3/$^{125}$I-ASM carriers, 2γ3/$^{125}$I-ASM carriers or 3γ3/$^{125}$I-ASM carriers were injected iv in C57Bl/6 mice. Blood samples were taken at 15 min and 30 min after injection, and the organs were collected 30 min after injection, to determine the presence of $^{125}$Iodine in the samples. (A) Percent of injected dose in circulation is shown for control IgG/$^{125}$I-ASM polystyrene carriers vs γ3/$^{125}$I-ASM carriers. (B) Percent of injected dose in liver (an organ of unspecific clearance) and lung (and organ requiring targeting for accumulation) are shown. (C) Mice were injected with either free $^{125}$I-ASM vs γ3/$^{125}$I-ASM carriers, 2γ3/$^{125}$I-ASM carriers or 3γ3/$^{125}$I-ASM carriers, blood and organs were collected 30 min after injection and the specificity index of all samples was calculated. Specificity index=Localization Ratio of the carrier divided by the Localization Ratio of the free enzyme, where the Localization Ratio is the percent injected dose/gram in an organ divided by percent injected dose/gram in blood. (D) Liver, lung, and brain uptake (30 min) of γ3/$^{125}$I-ASM polystyrene carriers compared to anti-ICAM/$^{125}$I-ASM carriers and control $^{125}$I-ASM. (E) Lung targeting of 2γ3/$^{125}$I-ASM polystyrene carriers vs 2γ3-scramble/$^{125}$I-ASM carriers in control C57Bl/6 mice (bars), and 2γ3/$^{125}$I-ASM carriers in ICAM-1 knock out (ICAM-1 KO) mice (line across the bar on the left). Mean±SEM; n=3 mice. (F) Transmission electron microscopy picture showing endocytosis of 2γ3/ASM PLGA carriers in lungs of mice (30 min post-injection). Asterisks=caveoli. EnC=Endothelial cell. EpC=Epithelial cell. Scale bar=100 nm.

Example 7

Therapeutic Effects of Cargoes Intracellularly Delivered to Patient Cells by γ3-Strategy Carriers Skin fibroblasts from type A Niemann-Pick patients were incubated overnight with BODIPY-FLC12-sphingomyelin to label sphingomyelin accumulation in lysosomes in these cells. Cells were then incubated with control media or treated for 5 h with recombinant ASM loaded on the surface of 100 nm polystyrene carriers or poly-lactic co-glycolic acid (PLGA) carriers targeted to ICAM-1 via either anti-ICAM monoclonal antibody or the peptide γ3. The cells were then washed, fixed, and stained with filipin to label cholesterol, which also accumulates intracellularly in Niemann-Pick disease. Samples were analyzed by fluorescence microscopy to determined the reduction of the levels of sphingomyelin and cholesterol. The percent of accumulation of these lipids was compared to that of untreated diseased cells (100% accumulation). Mean±SEM, n>20 cells.

TABLE 1

| | (% no treatment) | | |
|---|---|---|---|
| | Anti-ICAM/ASM polystyrene | γ3/ASM polystyrene | γ3/ASM PLGA |
| Sphingomyelin | 10 ± 1.7 | 10 ± 1.9 | 3 ± 1.3 |
| Cholesterol | 6 ± 1.0 | 5 ± 1.1 | 5 ± 0.7 |

Example 8

Design of a Chimeric Therapeutic Enzyme Containing ICAM-1-Targeting γ3, 2γ3 3γ3 or A1 Derivative Peptides The coding sequence for the peptides γ3, 2γ3, 3γ3 or A1 can be formed by hybridization of the forward (F) and reverse (R) oligonucleotides XmaI-ATG-γ3-SpeI, XmaI-ATG-2γ3-SpeI, XmaI-ATG-3γ3-SpeI, XmaI-ATG-B7-SpeI, XmaI-ATG-B8-SpeI, XmaI-ATG-B9-SpeI, XmaI-ATG-B10-SpeI, or XmaI-ATG-D6-SpeI, respectively. The coding sequence for spacer between these peptides and ASM can be formed by hybridization of the forward (F) and reverse (R) oligonucleotides SpeI-(Ser4Gly)2-EcoRI. ASM coding sequence can be amplified by PCR from a plasmid containing ASM cDNA, using the forward (F) primer EcoRI-ASM and reverse (R) primer ASM-XbaI. The resulting fragments can be cloned into pMT/BiP/V5-His (B) plasmid to obtain an ICAM-1-targeted ASM plasmid termed (B) (FIG. 7). (B) can be used for amplification in *E. coli* and expression in S2 cells, using single-site restriction enzyme digestion with XmaI, SpeI, EcoRI, and XbaI, respectively, and subsequent ligation.

Oligonucleotides:

XmaI-ATG-γ3-SpeI-F
(SEQ ID NO: 4)
5'-CCGGGATGAATAATCAAAAGATTGTTAACCTGAAAGAGAAGGTAGCCCAGCTTGAAGCAA-3'

XmaI-ATG-γ3-SpeI-R
(SEQ ID NO: 5)
5'-CTAGTTGCTTCAAGCTGGGCTACCTTCTCTTTCAGGTTAACAATCTTTTGATTATTCATC-3'

XmaI-ATG-2γ3-SpeI-F
(SEQ ID NO: 6)
5'-CCGGGATGAATAATCAAAAGATTGTTAACATCAAAGAGAAGGTAGCCCAGATCGAAGCAA-3'

XmaI-ATG-2γ3-SpeI-R
(SEQ ID NO: 7)
5'-CTAGTTTGCTTCGATCTGGGCTACCTTCTCTTTGATGTTAACAATCTTTTGATTATTCATC-3'

XmaI-ATG-3γ3-SpeI-F
(SEQ ID NO: 8)
5'-CCGGGATGAATAATCAAAAGCTTGTTAACATCAAAGAGAAGGTAGCCCAGATCGAAGCAA-3'

XmaI-ATG-3γ3-SpeI-R
(SEQ ID NO: 9)
5'-CTAGTTGCTTCGATCTGGGCTACCTTCTCTTTGATGTTAACAAGCTTTTGATTATTCATC-3'

XmaI-ATG-A1-SpeI-F
(SEQ ID NO: 20)
5'-CCGGGATGTACCCCGCCAGCTACCAGCGGA-3'

XmaI-ATG-A1-SpeI-R
(SEQ ID NO: 21)
5'-CTAGTCCGCTGGTAGCTGGCGGGGTACATCC-3'

XmaI-ATG-D6-SpeI-F
(SEQ ID NO: 22)
5'-CCGGGATGGGCTGCAAGCTGTGCGCCCAGA-3'

XmaI-ATG-D6-SpeI-R
(SEQ ID NO: 23)
5'-CTAGTCTGGGCGCACAGCTTGCAGCCCATC-3'

XmaI-ATG-B7-SpeI-F
(SEQ ID NO: 24)
5'-CCGGGATGTACCAGGCCACCCCCCTGCCCA-3'

XmaI-ATG-B7-SpeI-R
(SEQ ID NO: 25)
5'-CTAGTGGGCAGGGGGGTGGCCTGGTACATC-3'

-continued

XmaI-ATG-B8-SpeI-F (SEQ ID NO: 26)

5'-CCGGGATGGGCAGCCTGCTGAGCGCCGCCA-3'

XmaI-ATG-B8-SpeI-R (SEQ ID NO: 27)

5'-CTAGTGGCGGCGCTCAGCAGGCTGCCCATC-3'

XmaI-ATG-B9-SpeI-F (SEQ ID NO: 28)

5'-CCGGGATGTTCAGCCCCCACAGCCGGACCA-3'

XmaI-ATG-B9-SpeI-R (SEQ ID NO: 29)

5'-CTAGTGGTCCGGCTGTGGGGGCTGAACATC-3'

XmaI-ATG-B10-SpeI-F (SEQ ID NO: 30)

5'-CCGGGATGTACCCCTTCCTGCCCACCGCCA-3'

XmaI-ATG-B10-SpeI-R (SEQ ID NO: 31)

5'-CTAGTGGCGGTGGGCAGGAAGGGGTACATC-3'

SpeI-(Ser4Gly)2-EcoRI-F (SEQ ID NO: 10)

5'-ACTAGTTCTTCTTCTTCTGGCTCTTCTTCTTCTGGCGAATTC-3'

SpeI-(Ser4Gly)2-EcoRI-R (SEQ ID NO: 11)

5'-GAATTCGCCAGAAGAAGAAGAGCCAGAAGAAGAAGAACTAGT-3'

EcoRI-ASM-F (SEQ ID NO: 12)

5'-AATTCCCCCGCTACGGAGCGTCAC-3'

ASM-XbaI-R (SEQ ID NO: 13)

5'-CTAGACTAGCAAAACAGTGGCCTTG-3'

Example 9

In vivo Brain Transport of Therapeutic Carriers Targeted to ICAM-1 Via the Affinity Peptide 2γ3

Biocompatible PLGA carriers (100 nm diameter) were coated by surface absorption with the ICAM-1-targerting peptide 2γ3 and the recombinant enzyme acid sphingomyelinase (ASM), taken as an example for a therapeutic cargo. The resulting 2γ3/ASM PLGA carriers were injected intravenously in anesthetized C57Bl/6 mice. Three hours after injection, animals were euthanized under anesthesia, perfused and fixed though the left ventricle of the heart under ventilation, and the brain was isolated and processed for transmission electron microscopy.

Figure 2:
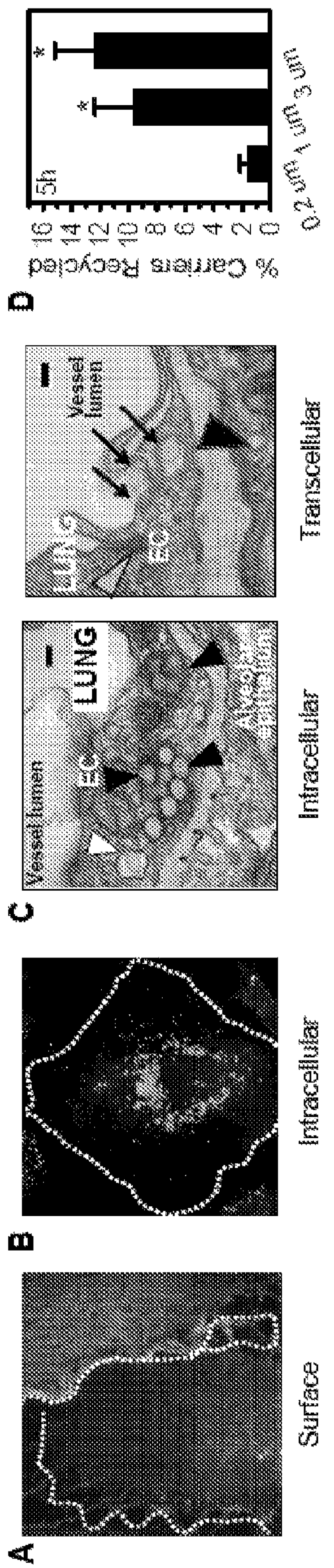
FIG. 2 illustrates the results of Example 2, where FIG. 2A-2C provide fluorescence and electron microscopy images of ICAM targeting by ICAM-1 specific targeting moieties
Figure 8A:
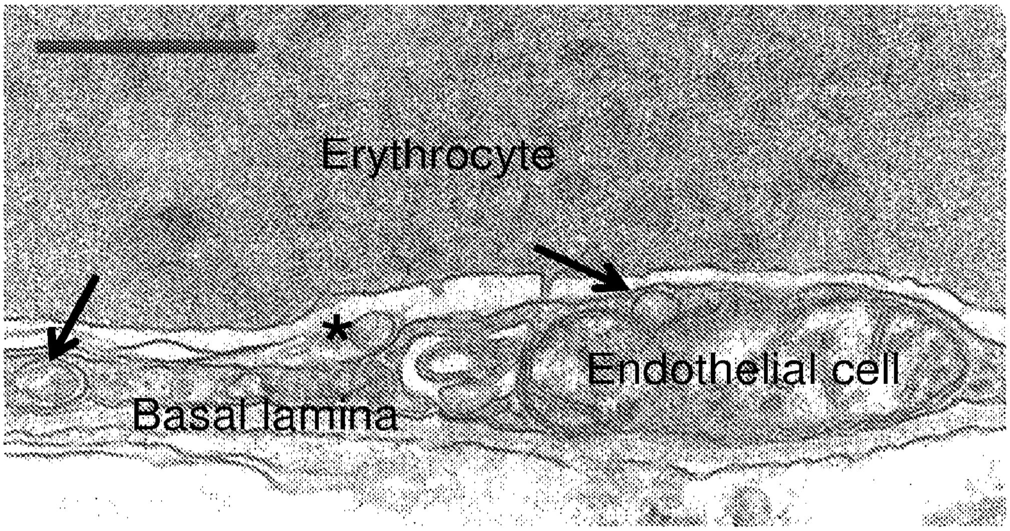
FIG. 8 is transmission electron microscopy images of the in vivo brain transport of compositions of the invention, as described in Example 9 hereof: (A) demonstrates delivery compositions bound to the surface of or endocytosed within vascular endothelial cells in the blood-brain barrier; and (B) demonstrates delivery compositions that have migrated across the blood-brain barrier into the brain.
Figure 8B:
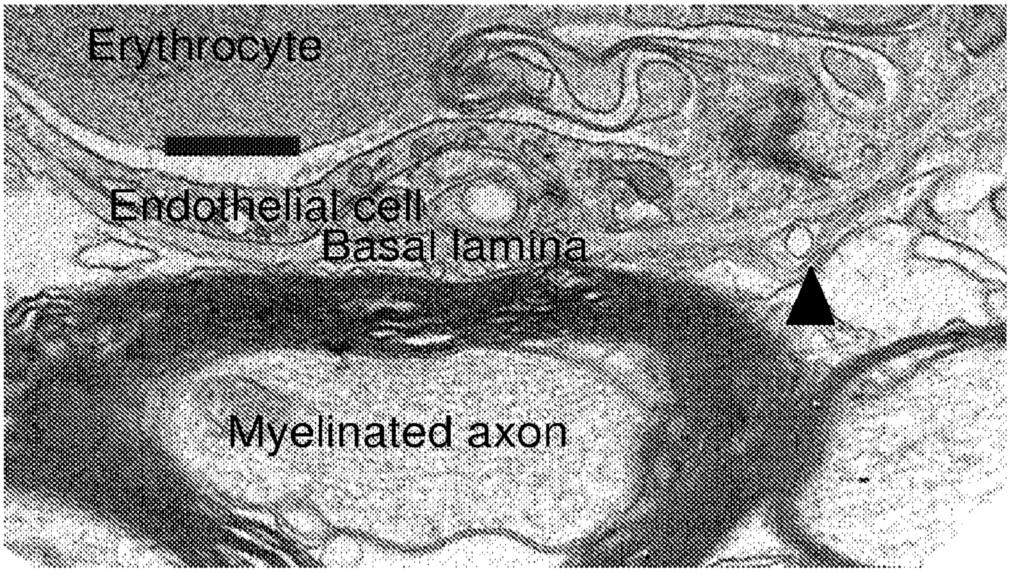

FIG. 8 provides transmission electron microscopy pictures showing biocompatible 2γ3/ASM PLGA carriers in brain of C57Bl/6 mice (3 h post-injection). Scale bar=500 nm. FIG. 8(A) 2γ3/ASM PLGA carriers bound to the surface of (asterisk) or endocytosed within (arrows) vascular endothelial cells in the blood-brain barrier FIG. 8(B) 2γ3/ASM PLGA carriers that have migrated across the blood-brain barrier into a region of the brain close to the myelinated axon of a neuron.

Example 10

Inhibition of Inflammatory Leukocyte Transmigration Across Endothelial Cells by ICAM-1 Targeting Peptides Human endothelial cells (human umbilical vein endothelial cells (HUVECs)) were grown until formation of a continuous confluent monolayer in a transwell filter located between upper and lower chambers. The cells were then treated with tumor necrosis factor alpha to mimic inflammatory activation of endothelial cells and SDF1a was added to the lower chamber to generate a gradient to attract white blood cells, as during inflammation. Lymphocytes isolated from human peripheral blood were activated with interleukin 2 and added to the upper chamber above endothelial cells in the absence (control) or presence of ICAM-1-targeting peptides A1, B7, B8, B9, B10, or D6. Albumin or a peptide of scrambled sequence were used as negative controls which should not block inflammatory transmigration of leukocytes across endothelial cells. The anti-ICAM antibody LB2, which is known to block leukocyte adhesion to ICAM-1, was used as a positive control which should block such transmigration.

Leukocytes which transmigrated to the lower chamber below endothelial cells were counted to assess their transmigration. FIG. 9 provides a graph of the resulting leukocyte transmigration as a percentage of the control. The peptides annotated with an asterisk in FIG. 9 indicate that the peptide was effective in statistically significant blockage of leukocyte transmigration across endothelial cells. All ICAM-1-targeting peptides tested were shown to inhibit transmigration of leukocytes in a specific and effective manner.

Example 11

In vivo of Lodging of Fibrin Microemboli in the Vasculature by ICAM-1 Targeting Peptides C57Bl/6 mice were first injected intravenously with γ3 to block ICAM-1 in the vascular endothelium in organs. Alternatively, injections of saline or anti-ICAM were used as controls. Fifteen minutes later the mice were injected with fibrin clots (microemboli around 3-5 micrometer) generated in the lab by established procedures.

Figure 10A:
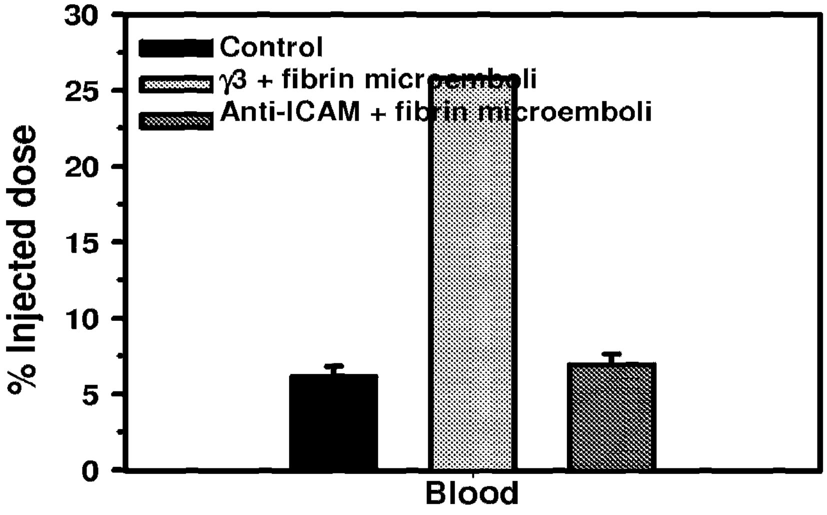
FIG. 10(A) is a graphical illustration of the amount of microemboli in circulation in blood, as evaluated at 1 min after injection
Figure 10B:
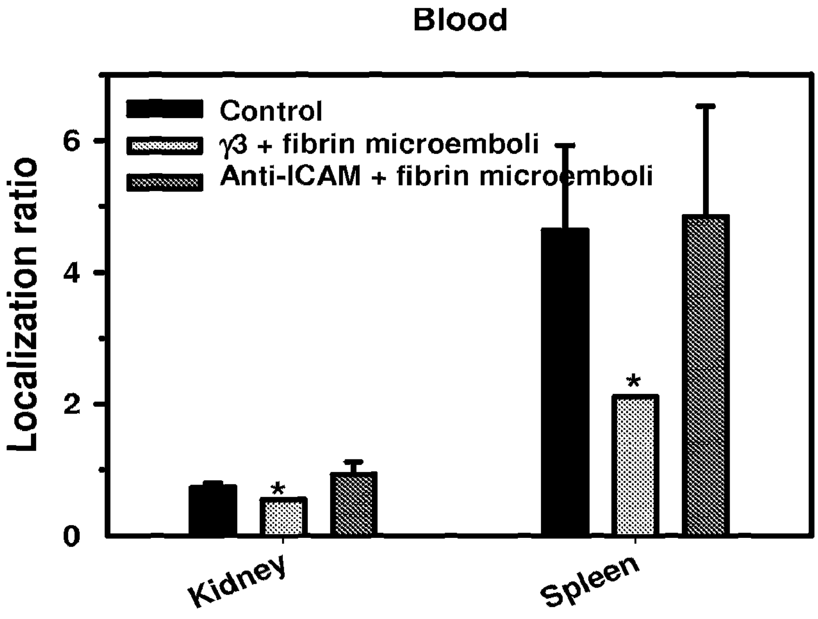
FIG. 10(B) is a graphical illustration of the amount of microemboli lodging in the vasculature of the kidneys and spleen at 15 min after injection, both as described in Example 11 herein.

Following microemboli administration, the microemboli amounts were measured in a gamma counter and calculated as percent of injected dose in circulation or localization ratio (the percent injected dose/gram in an organ divided by percent injected dose/gram in blood). FIG. 10(A) is a graphical illustration of the amount of microemboli in circulation in blood, as evaluated at 1 min after injection and FIG. 10(B) is a graphical illustration of the amount of microemboli lodging in the vasculature of the kidneys and spleen at 15 min after injection.

In contrast to anti-ICAM, blocking of ICAM-1 with γ3 peptide caused fibrin microemboli to remain in circulation, attenuating microemboli lodging in organs.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A delivery composition for delivery of an agent into a cell, the composition comprising:

a) a targeting moiety comprising a peptide or protein having a sequence selected from the group consisting of SEQ ID NO: 2, SEQ ID NO: 3, SEQ ID NO: 14, SEQ ID NO: 15, SEQ ID NO: 16, SEQ ID NO: 17, SEQ ID NO: 18, and SEQ ID NO: 19; and an agent; or b) a nucleic acid having a sequence encoding a targeting moiety having a sequence B selected from the group consisting of SEQ ID NO: 2, SEQ ID NO: 3, SEQ ID NO: 14, SEQ ID NO: 15, SEQ ID NO: 16, SEQ ID NO: 17, SEQ ID NO: 18, and SEQ ID NO: 19; and a second nucleic acid having a sequence encoding an agent, wherein the targeting moiety recognizes and binds to a target on the cell, and is effective to deliver the agent into the cell.

2. The delivery composition of claim 1, wherein the agent comprises any of a biologically active compound, an imaging compound, a monitoring compound, therapeutic compound, a diagnostic compound, an enzyme, a peptide, a protein, a lipid, a lipoprotein, a sugar, a hormone, a vitamin, a nucleic acid, a virus, a bacteria, and a cell.

3. The delivery composition of claim 2, wherein the agent comprises a lysosomal enzyme.

4. The delivery composition of claim 3, wherein the agent comprises any of the enzymes involved in Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, infantile neuronal ceroid lipofuscinosis, and prosaposin.

5. The delivery composition of claim 1, wherein the agent comprises acid sphingomyelinase.

6. The delivery composition of claim 1, wherein the target on the cell comprises ICAM-1.

7. The delivery composition of claim 6, wherein the ICAM-1 comprises human or mouse ICAM-1.

8. The delivery composition of claim 1, wherein delivery of the agent to the cell comprises any of intracellular transport and transcellular transport of the agent.

9. The delivery composition of claim 1, further comprising a second targeting moiety.

10. The delivery composition of claim 9, wherein the second targeting moiety comprises a moiety selected from an antibody, an aptamer, a nucleic acid, a peptide, a carbohydrate, a lipid, a vitamin, a toxin, a component of a microorganism, a hormone, and a receptor ligand.

11. The delivery composition of claim 1, further comprising a delivery carrier.

12. The delivery composition of claim 11, wherein the delivery carrier comprises a carrier species selected from a natural virus or derived viral-like particle, dendrimer, carbon nanoassembly, liposome, a polymer carrier, a microbubble, a paramagnetic particle, a ferromagnetic particle, a self-assembled polymer, a polymersome, a filomicelle, a micelle, a micro particle or nanoparticle, an albumin particle, and a lipoprotein.

13. The delivery composition of claim 1, wherein the target organ is selected from kidney, spleen, heart, lung, liver, and brain.

14. A method for delivering an agent into a cell, the method comprising administration of a delivery composition of claim 1.

15. A method for delivering an agent to the surface of a cell, the method comprising administration of a delivery composition comprising:

a) a targeting moiety comprising a peptide or protein having a sequence selected from the group consisting of SEQ ID NO: 2, SEQ ID NO: 3, SEQ ID NO: 14, SEQ ID NO: 15, SEQ ID NO: 16, SEQ ID NO: 17, SEQ ID NO: 18, and SEQ ID NO: 19; and an agent; or b) a nucleic acid having a sequence encoding a targeting moiety having a sequence selected from the group consisting of SEQ ID NO: 2, SEQ ID NO: 3, SEQ ID NO: 14, SEQ ID NO: 15, SEQ ID NO: 16, SEQ ID NO: 17, SEQ ID NO: 18, and SEQ ID NO: 19; and a second nucleic acid having a sequence encoding an agent.

16. A method for delivering an agent into a cell, the method comprising administration of a delivery composition comprising:

a) a targeting moiety comprising a peptide or protein having a sequence selected from the group consisting of SEQ ID NO: 2, SEQ ID NO: 3, SEQ ID NO: 14, SEQ ID NO: 15, SEQ ID NO: 16, SEQ ID NO: 17, SEQ ID NO: 18, and SEQ ID NO: 19; and an agent; or b) a nucleic acid having a sequence encoding a targeting moiety having a sequence selected from the group consisting of SEQ ID NO: 2, SEQ ID NO: 3, SEQ ID NO: 14, SEQ ID NO: 15, SEQ ID NO: 16, SEQ ID NO: 17, SEQ ID NO: 18, and SEQ ID NO: 19; and a second nucleic acid having a sequence encoding an agent, and further comprising a delivery carrier, wherein the targeting moiety recognizes and binds to a target on the cell, and the composition is effective to deliver the agent into the cell.

17. The method of claim 16, wherein the delivery carrier comprises a carrier species selected from a natural virus or derived viral-like particle, dendrimer, carbon nanoassembly, liposome, a polymer carrier, a microbubble, a paramagnetic particle, a ferromagnetic particle, a self-assembled polymer, a polymersome, a filomicelle, a micelle, a micro particle or nanoparticle, an albumin particle, and a lipoprotein.

18. The method of claim 17, wherein the delivery carrier comprises a polymer carrier.

19. The method of claim 18, wherein the delivery carrier is a polystyrene carrier or a poly-lactic co-glycolic acid carrier.

20. The method of claim 16, wherein a delivery composition is administered comprising a targeting moiety comprising a peptide or protein having a sequence selected from the group consisting of SEQ ID NO: 2, SEQ ID NO: 3, SEQ ID NO: 14, SEQ ID NO: 15, SEQ ID NO: 16, SEQ ID NO: 17, SEQ ID NO: 18, and SEQ ID NO: 19; and an agent.

21. The method of claim 16, wherein a delivery composition is administered comprising a nucleic acid having a sequence encoding a targeting moiety having a sequence selected from the group consisting of SEQ ID NO: 2, SEQ ID NO: 3, SEQ ID NO: 14, SEQ ID NO: 15, SEQ ID NO: 16, SEQ ID NO: 17, SEQ ID NO: 18, and SEQ ID NO: 19; and a second nucleic acid having a sequence encoding an agent.

22. The method of claim 16, wherein the targeting moiety is coupled to the delivery carrier.

* * * * *

UNITED STATES PATENT AND TRADEMARK OFFICE

CERTIFICATE OF CORRECTION

PATENT NO. : 8,926,946 B2
APPLICATION NO. : 13/376362
DATED : January 6, 2015
INVENTOR(S) : Silvia Muro Galindo et al.

It is certified that error appears in the above-identified patent and that said Letters Patent is hereby corrected as shown below:

Title Page, Item 75, Inventors: “Ming Meng, Baoding (CN)” should be -- Ming Meng, Hebei (CN) --.

IN THE CLAIMS:

Column 37, line 25: “moiety having a sequence B selected from the group” should be
-- moiety having a sequence selected from the group --

Signed and Sealed this
Thirty-first Day of March, 2015

Michelle K. Lee
*Director of the United States Patent and Trademark Office*